(12) United States Patent
Shin et al.

(10) Patent No.: US 11,642,007 B2
(45) Date of Patent: May 9, 2023

(54) DETACHABLE ENDOSCOPE HAVING WIRE BUFFER FUNCTION

(71) Applicant: TAEWOONG MEDICAL CO., LTD., Gimpo-si (KR)

(72) Inventors: Kyong Min Shin, Gyeonggi-do (KR); Sung Hwan Park, Gimpo-si (KR); Hyun Soo Ji, Gimpo-si (KR)

(73) Assignee: TAEWOONG MEDICAL CO., LTD., Gimpo-si (KR)

( * ) Notice: Subject to any disclaimer, the term of this patent is extended or adjusted under 35 U.S.C. 154(b) by 302 days.

(21) Appl. No.: 17/014,150

(22) Filed: Sep. 8, 2020

(65) Prior Publication Data

US 2021/0068625 A1    Mar. 11, 2021

(30) Foreign Application Priority Data

Sep. 11, 2019    (KR) .................... 10-2019-0112951

(51) Int. Cl.
*A61B 1/00* (2006.01)
*A61B 1/005* (2006.01)
*A61B 1/05* (2006.01)

(52) U.S. Cl.
CPC ........ *A61B 1/00105* (2013.01); *A61B 1/0052* (2013.01); *A61B 1/0057* (2013.01); *A61B 1/00121* (2013.01); *A61B 1/05* (2013.01)

(58) Field of Classification Search
CPC ..... A61B 1/00105; A61B 1/0052; A61B 1/05; A61B 1/0057; A61B 1/00121
See application file for complete search history.

(56) References Cited

U.S. PATENT DOCUMENTS

| 4,203,430 A | * | 5/1980 | Takahashi | ............ | A61B 1/0052 600/149 |
| 5,359,994 A | * | 11/1994 | Krauter | ................ | A61B 1/0052 604/95.04 |
| 2008/0125628 A1 | * | 5/2008 | Ueno | ................... | A61B 1/0052 600/130 |

(Continued)

FOREIGN PATENT DOCUMENTS

| JP | H03-111024 A | 5/1991 |
| JP | 2000-014628 A | 1/2000 |
| JP | 2009-142562 A | 7/2009 |

(Continued)

*Primary Examiner* — Anh Tuan T Nguyen
*Assistant Examiner* — Rynae E Boler
(74) *Attorney, Agent, or Firm* — Bridgeway IP Law Group, PLLC; Jihun Kim

(57) ABSTRACT

A detachable endoscope having a buffer function includes: an operation part for operating the front end of an insertion part having an illuminating photographing part to be bent and a detachable unit for detachably coupling the insertion part and the operation part, wherein the detachable unit includes: a first detachable module connected to the respective other ends of first, second, third, and fourth operation wires having the respective one ends connected to the front end inside the insertion part and provided on the rear end of the insertion part, and a second detachable module connected to first, second, third, and fourth connection wires of a direction conversion part for converting a rotational motion into a linear motion in the operation part and provided on the front end of the operation part.

14 Claims, 25 Drawing Sheets

(56) References Cited

U.S. PATENT DOCUMENTS

2014/0107416 A1    4/2014  Birnkrant

FOREIGN PATENT DOCUMENTS

| JP | 2010-051543 A | 3/2010 |
| JP | 2010-194102 A | 9/2010 |
| JP | 2011-177383 A | 9/2011 |
| JP | 2013-248118 A | 12/2013 |
| KR | 10-0673412 B1 | 1/2007 |
| KR | 10-2011-0060785 A | 6/2011 |
| KR | 10-1091999 B1 | 12/2011 |
| KR | 10-1783225 B1 | 9/2017 |

* cited by examiner

DETACHABLE ENDOSCOPE HAVING WIRE BUFFER FUNCTION

TECHNICAL FIELD

The present disclosure relates to an endoscope, and more specifically, to a detachable endoscope having a wire buffer function, which may equally align the respective ends of a connected structure of an operation part and a corresponding connecting structure at constant locations of the end of an insertion part at all times regardless of a length error caused by a curved deformation portion generated on the middle portion of the length of the insertion part, and perform an operation of operating of selectively locking and connecting a connecting port of the insertion part and a connected port of the operation part and an operation of operating the front end of the insertion part to be bent vertically or horizontally in conjunction with each other.

BACKGROUND ART

Generally, in a surgery using an endoscope, a camera-installed endoscope and a surgical tool are inserted through a small hole without largely incising a human body, and then the surgery is conducted while examining a patient's affected area through the image photographed by the endoscope in a body.

Particularly, the endoscopic surgery starting from laparoscopic surgery has an advantage in that the scar area is small and the bleeding is also less because an incision site is small compared to laparotomy, so that a recovery time of the patient is short after the surgery.

Recently, not only the technology has been developed to enable the endoscopic surgery for almost all surgeries requiring laparotomy, but also the endoscopic surgery is increasingly applied in other medical fields.

A conventional general endoscope is integrally composed of an insertion part inserted into the human body and an operation part for controlling the insertion part, and a plurality of pipelines and guides are embedded therein through the inside of each part, and particularly, since an imaging element such as an expensive CCD or the like is provided on the front end of the insertion part inserted into the body, there is a problem in that it is difficult to separate only the insertion part from the operation part to be replaced with new one.

(Patent Document 1) KR10-0673412B1
(Patent Document 2) KR10-1091999B1
(Patent Document 3) KR10-1783225B1

Patent Documents 1 to 3 disclose various types of detachable endoscopes which may couple and use the insertion part inserted into the body and the operation part for operating the insertion part or separate and store the insertion part and the operation part according to the trend of further strengthening the hygiene function of the endoscope used for medical use in recent years.

When the insertion part completely separated from the operation part is rolled in a substantially circular shape to be stored or the middle portion of the length of the insertion part is forcibly and curvedly deformed by an external factor to be bent in the detachable endoscopes disclosed in these Patent Documents, at least one curved deformation portion is formed on the middle portion of the length of the insertion part which has the plurality of wires arranged parallel to each other in the longitudinal direction disposed in the inner space.

At this time, the inner curved portion and the outer curved portion are formed on the inside and outside of the curved deformation portion, respectively, and the outer radius of curvature formed by the outer curved portion based on a virtual reference point is formed larger than the inner radius of curvature formed by the inner curved portion, thereby forming the condition in which the radius of curvature of the wire adjacent to the outer curved portion becomes larger than the radius of curvature of the wire adjacent to the inner curved portion.

That is, when at least one curved deformation portion is generated in the middle portion of the length of the insertion part, a length error occurs in which the locations of the respective other ends of the plurality of wires with the respective one ends constrained inside the front end of the insertion part are different from each other.

In this case, since the connection structure corresponding to the wire adjacent to the outer curved portion among the plurality of connection structures provided on the respective other ends of the plurality of wires which cause the length error caused by the curved deformation portion is located to enter the inside of the insertion part by the length error compared to the other end of another connection structure corresponding to the wire close to the inner curved portion, the plurality of connection structures are aligned at different locations, respectively.

Under these conditions, since the user needs to perform the work of coupling the insertion part and the operation part in the state of linearly maintaining the insertion part at all times so that the curved deformation portion causing the length error is not generated on the middle portion of the length of the insertion part in order to couple the connected structure of the operation to the connecting structure of the insertion part to connect the connected structure to the connecting structure, the preliminary preparation work and conditions for coupling the detachable endoscope are very cumbersome, and the connection failure between the connecting structure and the connected structure frequently occurs, thereby resulting in inconvenience in use.

In addition, if the end of the connecting structure of the insertion part is forcibly constrained by a separate constrain structure so as not to enter into the insertion part due to at least one curved deformation portion generated in the middle portion of the length of the insertion part, there is a problem in that the stretched deformation occurs in which the wires are stretched by the tension applied to the wires located on the inner and outer curved portions upon the generation of the curved deformation portion, thereby not precisely performing the operation of displacing the front end of the insertion part to be bent vertically and horizontally.

Particularly, since the tension applied to the wire adjacent to the outer curved portion is formed to be relatively large, there is a fatal problem in that the stretched deformation of the wire becomes excessive and the middle portion of the length of the wire is disconnected, thereby losing the endoscope function.

DISCLOSURE

Technical Problem

Therefore, the present disclosure is intended to solve the aforementioned problems, and an object of the present disclosure is to provide a detachable endoscope having a buffer function, which may equally align the respective ends of a connected structure of an operation part and a corresponding connecting structure at constant locations of the end of an insertion part at all times regardless of a length error caused by a curved deformation portion generated on the middle portion of the length of the insertion part.

In addition, another object of the present disclosure is to a detachable endoscope having a buffer function, which may perform an operation of selectively locking and connecting a connecting port of an insertion part to a connected port of an operation part upon selective rotation of the operation part and an operation of operating the front end of the insertion part to be bent vertically or horizontally in conjunction with each other, thereby increasing convenience in use.

The objects to be achieved in the present disclosure are not limited to the aforementioned objects, and other objects not mentioned will be clearly understood by those skilled in the art to which the present disclosure pertains from the following description.

Technical Solution

As a specific means for achieving the objects, a preferred exemplary embodiment of the present disclosure provides a detachable endoscope having a buffer function, the detachable endoscope including: an operation part for operating the front end of an insertion part having an illuminating photographing part to be bent and a detachable unit for detachably coupling the insertion part and the operation part, in which the detachable unit includes: a first detachable module connected to the respective other ends of first, second, third, and fourth operation wires having the respective one ends connected to the front end inside the insertion part and provided on the rear end of the insertion part, and a second detachable module connected to first, second, third, and fourth connection wires of a direction conversion part for converting a rotational motion into a linear motion in the operation part and provided on the front end of the operation part, the first detachable module includes: a first module main body having first, second, third, and fourth linear guide holes formed to penetrate the insides thereof in a longitudinal direction, and having a central placement hole formed to penetrate the inside thereof in a thickness direction, first, second, third, and fourth rack gears having the respective one ends correspondingly connected to the first, second, third, and fourth operation wires via a first buffer part and assembled in the first, second, third, and fourth linear guide holes, a first pinion gear gear-engaged between the first and second rack gears, a second pinion gear gear-engaged between the third and fourth rack gears, and a gear shaft having the first and second pinion gears assembled with a vertical predetermined interval and fixedly installed in the central placement hole, and the first buffer part includes: a first buffer body integrally provided on the respective ends of the first, second, third, and fourth operation wires, a first buffer line hole having a predetermined length formed inside the respective one ends of the first, second, third, and fourth rack gears and having the first buffer body reciprocatably inserted and disposed therein, and a first buffer stopper forming an inner hole having the operation wire having the first buffer body disposed to penetrate the inside thereof and assembled on the opened end of the first buffer line hole so as to prevent the first buffer body from being separated to the outside, thereby compensating length errors of the first, second, third, and fourth operation wires caused by curved deformation portions generated on the middle portion of the length of the insertion part separated from the operation part by the first buffer part to align and dispose first, second, third, and fourth connecting ports provided on the ends of the first, second, third, and fourth rack gears at the same locations of the end of the first detachable module.

At this time, the first buffer stopper may be provided in a hollow cylindrical body forming a slit cutout in a longitudinal direction.

At this time, the first buffer stopper may have a fixing part having an assembling hole having a fastening member fastened to a fastening hole formed in the end of each of the first, second, third, and fourth rack gears disposed to penetrate the inside thereof.

At this time, the inner surface of an inlet end of the first buffer line hole may be in contact with the end of the first buffer stopper, and may have a first inner projection having an annular shape forming a circular hole through which the first buffer body may pass.

At this time, the first, second, third, and fourth rack gears may include: linear bars having predetermined lengths slidably assembled in the first, second, third, and fourth linear guide holes, and linear gear teeth formed to protrude from the linear bars so as to be gear-engaged with circular gear teeth formed on the outer circumferential surfaces of the first and second pinion gears.

At this time, the respective linear bars of the first, second, third, and fourth rack gears may include: movable bodies guided and moved along a plurality of linear-type guide slits formed to be cutout on both side surfaces of the first module main body.

At this time, the gear shaft may have first and second ring-type grooves recessed on the outer circumferential surfaces corresponding to the first and second pinion gears, and the first and second ring-type grooves may have first and second elastic rings elastically contacting the inner circumferential surfaces and the outer circumferential surfaces of the first and second pinion gears.

At this time, the first detachable module may include: a wire support part for supporting linear motions of the first, second, third, and fourth operation wires, and the wire support part may have first, second, third, and fourth support bodies having support holes, into which the first, second, third, and fourth operation wires are correspondingly inserted, formed to penetrate the insides thereof, a support block for fixedly installing the first, second, third, and fourth support bodies on one ends thereof, and a connection bracket for assembling the support block on one end of the first module main body.

In addition, a preferred exemplary embodiment of the present disclosure provides a detachable endoscope having a wire buffer function, the detachable endoscope including: an operation part for operating the front end of an insertion part having an illuminating photographing part to be bent and a detachable unit for detachably coupling the insertion part and the operation part, in which the detachable unit includes: a first detachable module connected to the respective other ends of first, second, third, and fourth operation wires having the respective one ends connected to the front end inside the insertion part and provided on the rear end of the insertion part, and a second detachable module connected to first, second, third, and fourth connection wires of a direction conversion part for converting a rotational motion into a linear motion in the operation part and provided on the front end of the operation part, the second detachable module includes: a second module main body having first, second, third, and fourth linear through holes formed to penetrate the insides thereof in a longitudinal direction and disposed inside the front end of the operation part, first, second, third, and fourth connection shafts having the respective one ends correspondingly coupled to the first, second, third, and fourth connection wires via a second buffer part and reciprocatably provided in the first, second, third, and fourth linear through holes, and first, second, third, and fourth connected ports selectively locked and connected to first, second, third, and fourth connecting ports provided on the first detachable module on the other ends of the first, second, third, and fourth connection shafts, the second buffer part includes: a second buffer body integrally provided on the respective ends of the first, second, third, and fourth connection wires, a second buffer line hole having a predetermined length formed inside the respective one ends of the first, second, third, and fourth connection shafts so that the second buffer body is reciprocatably inserted and disposed therein, and a second buffer stopper assembled on the opened end of the second buffer line hole to prevent the second buffer body from being separated to the outside, and upon the selective rotation of the operation part, one of the first, second, third, and fourth connection shafts is pulled and moved toward the operation part by the interference between the second buffer body and the second buffer stopper, and the remaining connection shafts stand by and stop inside the front end of the operation part, thereby selectively locking and connecting any one of the first, second, third, and fourth connecting ports of the first detachable module to any one of the first, second, third, and fourth connected ports of the second detachable module.

At this time, the inner surface of an inlet end of the second buffer line hole may be in contact with the end of the second buffer stopper, and may have a second inner projection having an annular shape forming a circular hole through which the second buffer body may pass.

At this time, the first, second, third, and fourth connection shafts may include: operation bars reciprocatably inserted into and disposed in the first, second, third, and fourth linear through holes, and having at least one elastic body, guide pins provided on one end of the operation bar so as to rotationally displace the operation bars while being curvedly guided and moved along composite guide slits formed to be cutout on the second module main body, and first, second, third, and fourth connected ports provided on one ends of the operation bars, on which the guide pins are provided, so as to be selectively locked and connected to the first, second, third, and fourth connecting ports.

At this time, the second module main body may include: a main body block having the first, second, third, and fourth linear through holes formed to penetrate the insides of bodies, and formed to have the composite guide slits formed to be cutout on the outer surfaces thereof, a first cover plate having a plurality of first entry and exit holes, through which the respective one ends of the first, second, third, and fourth connection shafts enter and exit, formed to penetrate the inside thereof and provided on one end of the main body block, and a second cover plate having a plurality of second entry and exit holes corresponding to the first, second, third, and fourth linear through holes formed to penetrate the inside thereof and provided on the other end of the main body block.

At this time, the elastic body may be supported by having one end contacting the first cover plate, and having the other end contacting a large diameter portion of the operation bar in which the guide pin is provided.

At this time, the composite guide slit may include: a curved section composed of a curved slit curvedly extending from both side surfaces of the main body block to the upper and lower surfaces thereof, and a linear section composed of a linear slit linearly extending from the upper and lower surfaces of the main body block.

At this time, the first, second, third, and fourth connected ports may include: slot-type locking holes exposing the inner cavity portions toward the first, second, third, and fourth connecting ports, and the first, second, third, and fourth connecting ports may include: locking pieces having the front ends spread to both sides thereof.

Advantageous Effects

The preferred exemplary embodiment of the present disclosure described above has the following effects.

The first, second, third, and fourth operation wires of the insertion part may be connected to the first, second, third, and fourth rack gears provided in the first detachable module via the first buffer part to equally align the respective ends of the connected port of the operation part and the corresponding connecting port of the insertion part at constant locations of the end of the insertion part at all times regardless of the length error caused by the curved deformation portion generated on the middle portion of the length of the separated insertion part upon storing and handling the insertion part separated from the operation part, thereby smoothly performing the correspondingly coupling between the connecting port and the connected port without locking failure upon coupling between the operation part and the insertion part.

The first, second, third, and fourth connection wires of the operation part may be connected to the first, second, third, and fourth connection shafts provided in the second detachable module via the second buffer part, and thus another connection shaft corresponding to the connection shaft pulled and moved by the second buffer part upon selective rotation of the operation part stands by and stops inside the front end of the operation part, thereby performing the selective locking-connection between any one of the first, second, third, and fourth connecting ports of the first detachable module and any one of the first, second, third, and fourth connected ports of the second detachable module, and performing the operation of operating the front end of the insertion part to be bent vertically or horizontally while performing the locking-connection between the corresponding connecting port and connected port in conjunction with each other.

BEST MODE

Figure 1:
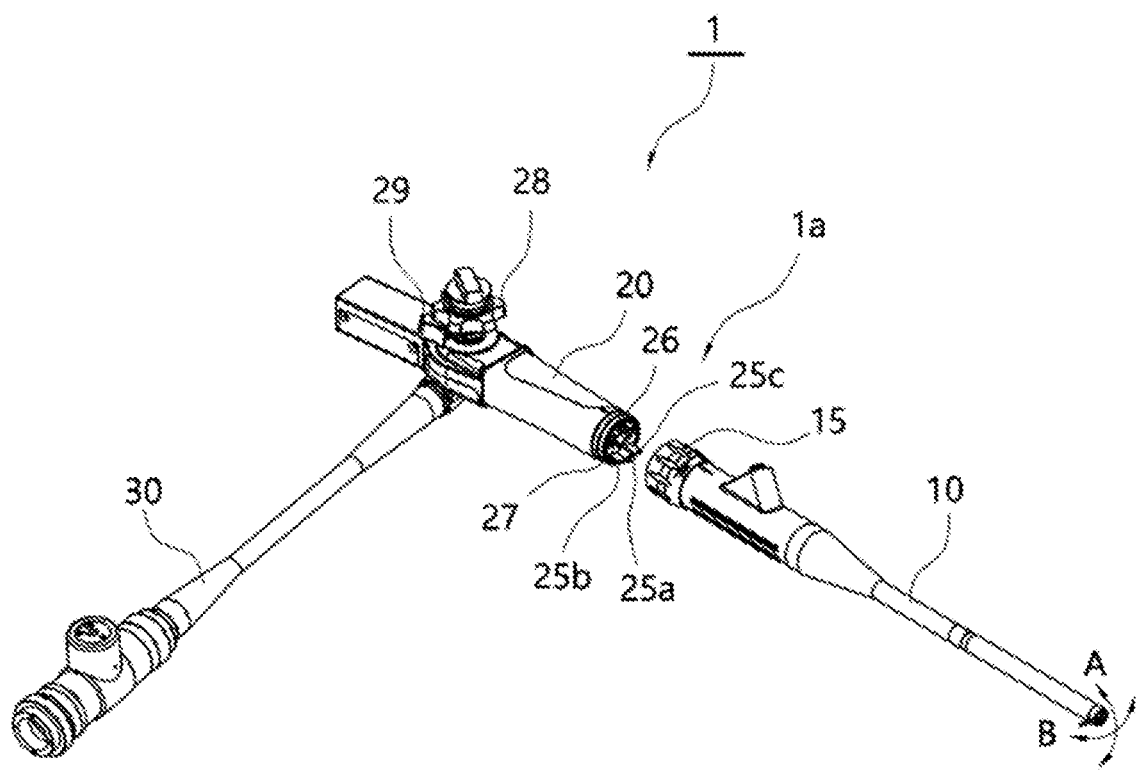
FIG. 1 is a perspective diagram illustrating an overall detachable endoscope having a wire buffer function according to an exemplary embodiment of the present disclosure.

Hereinafter, preferred exemplary embodiments of the present disclosure will be described in detail with reference to the accompanying drawings so that those skilled in the art to which the present disclosure pertains may easily practice the present disclosure. However, in specifically describing a structural principle of the preferred exemplary embodiments of the present disclosure, detailed descriptions of the related and known functions or components will be omitted if it is determined that the detailed descriptions thereof may unnecessarily obscure the gist of the present disclosure.

In addition, the same reference numerals are used for the parts having similar functions and operations throughout the drawings.

In addition, throughout the specification, when a part is said to be 'connected' to another part, the part is not only 'directly connected' to another part, but also 'indirectly connected' to another part with other elements interposed therebetween. In addition, the term 'including' a component means that other components may be further included, rather than excluding other components, unless specially stated otherwise.

As illustrated in FIG. 1, a detachable endoscope 1 according to an exemplary embodiment of the present disclosure includes an insertion part 10 having the front end inserted into a body upon endoscopic surgery, an operation part 20 having a plurality of operation handles, an universal joint 30 electrically connected to an endoscope control management system, and a detachable unit 1a for coupling the insertion part 10 to the operation part 20 to mechanically connect the insertion part to the operation part before the endoscopic surgery or separating the insertion part 10 and the operation part 20 after the endoscopic surgery.

The insertion part 10 is made of a flexible tube material to adjust a direction in which the insertion part 10 is inserted into the body, and has a lighting photographing part having a light source for illuminating the body and an image sensor for photographing the in-body on the front end thereof.

The operation part 20 has an upper operation handle 28 for operating the front end of the insertion part inserted into the body to be bent vertically and a lower operation handle 29 for operating the front end of the insertion part to be bent horizontally.

The inside of the operation part 20 has a direction conversion part which has upper and lower sprockets provided in the upper and lower operation handles, respectively, and upper and lower chains connected to the upper and lower sprockets to convert rotational motions of the upper and lower sprockets into linear motions of the upper and lower chains upon operations of the upper and lower operation handles, thereby converting the selective rotational motions of the upper and lower operation handles into the linear motions, and the upper and lower chains are connected to the inner end of the front end of the insertion part via a plurality of operation wires disposed inside the insertion part.

By converting some of the plurality of operation wires disposed in the insertion part into the linear motions through the upper and lower sprockets rotated by the selective rotations of the upper and lower operation handles by the user and the upper and lower chains which linearly reciprocate, the front end of the insertion part is bent vertically or horizontally in the body according to the linear motion of the operation wire.

The operation part has an operation switch and an operation button for putting or discharging liquid and gas for cleaning and disinfection upon endoscopic surgery, and the rear end of the insertion part detachably assembled with the front end of the operation part via the detachable unit is provided with a doorway through which a surgical element, such as an endoscopic treatment element having a clip, enters into and exits from the insertion part and a cap for opening and closing the doorway.

Figure 2:
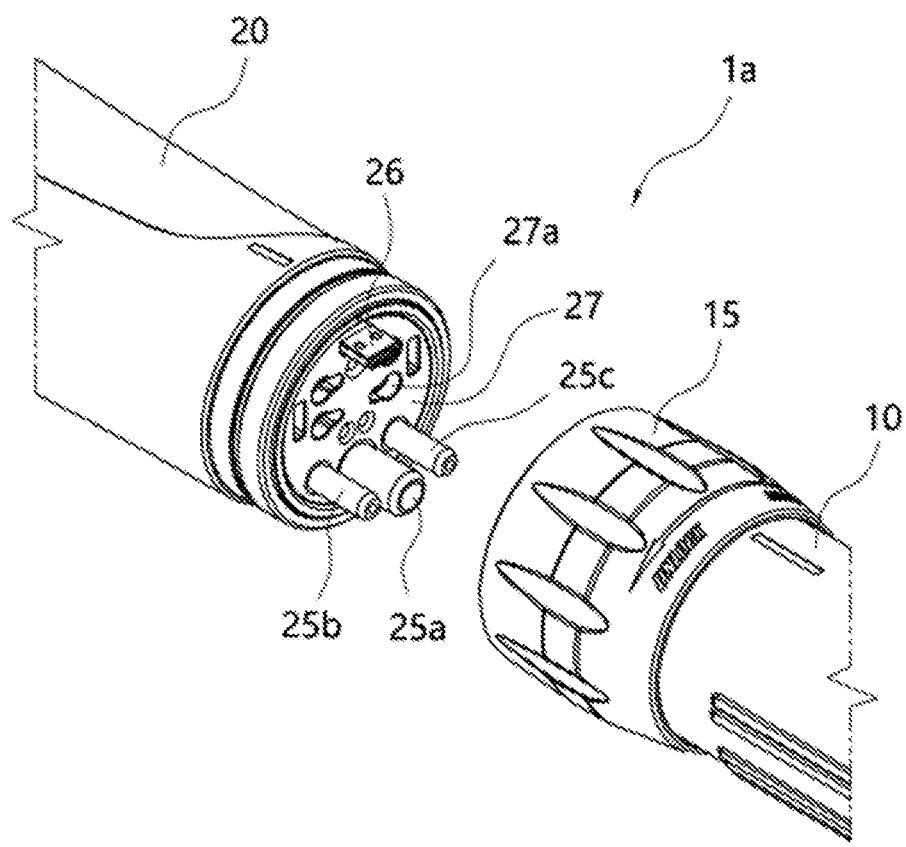
FIG. 2 is an enlarged diagram illustrating a coupling portion between an insertion part and an operation part of the detachable endoscope having the wire buffer function according to the exemplary embodiment of the present disclosure.

In FIGS. 1 and 2, an end cover 27 provided on the end of the operation part has an air supply channel 25b for supplying air, a water supply channel 25c for supplying water, and a suction channel 25a for sucking water and air to discharge the water and the air to the outside, and has a terminal 26 electrically connected to a lighting photographing part, whereas the rear end of the insertion part 10 made of a substantially cylindrical housing has a ring-type coupling body 15 screw-coupled to a female screw part formed on the front end of the operation part 20 formed of a cylindrical housing.

Figure 3:
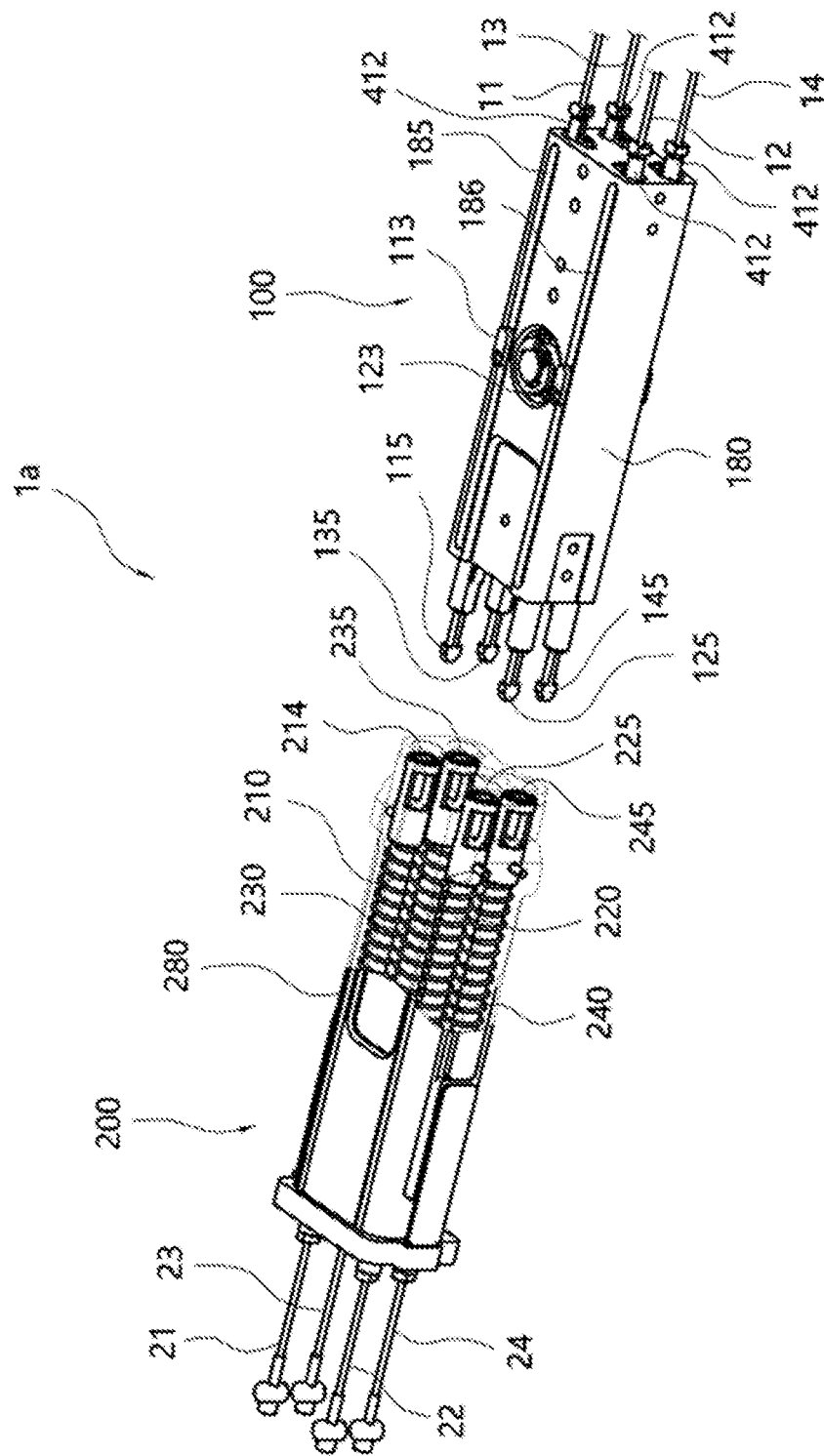
FIG. 3 is a perspective diagram illustrating a detachable unit provided in the detachable endoscope having the wire buffer function according to the exemplary embodiment of the present disclosure.

As illustrated in FIGS. 2 and 3, the detachable endoscope 1 according to the preferred exemplary embodiment of the present disclosure includes the detachable unit 1a for detachably coupling the rear end of the insertion part 10 and the front end of the operation part 20.

The detachable unit 1a includes a first detachable module 100 inserted into and disposed in the insertion part, a second detachable module 200 inserted into and disposed in the operation part and correspondingly coupled to the first detachable module, and first and second buffer parts 410, 420.

The first detachable module 100 is connected to the respective one ends of first and second operation wires 11, 12 disposed inside the insertion part parallel to each other to operate the front end of the insertion part to be bent vertically (A), and connected to the respective one ends of third and fourth operation wires 13, 14 disposed inside the insertion part parallel to each other to operate the front end of the insertion part to be bent horizontally (B).

The second detachable module 200 is connected to both ends of each of the upper and lower chains wound around the upper and lower sprockets rotated forward and backward by the upper and lower operation handles 28, 29 via first, second, third, and fourth connection wires 21, 22, 23, 24.

The first buffer part 410 gives a buffer function to a portion connecting the first, second, third, and fourth operation wires 11, 12, 13, 14 of the insertion part to the first, second, third, and fourth rack gears 110, 120, 130, 140 provided in the first detachable module 100, and the second buffer part 420 gives a buffer function to a portion connecting the first, second, third, and fourth operation wires 21, 22, 23, 24 of the operation part to the first, second, third, and fourth connection shafts 210, 220, 230, 240 provided in the second detachable module 200.

Here, although it has been illustrated and described that the first and second connection wires 21, 22 connected to both ends of the upper chain wound around the upper sprocket operate the front end of the insertion part to be bent vertically in conjunction with a pair of the first and second operation wires 11, 12 disposed parallel to each other on the upper side inside the insertion part in the figure, whereas the third and fourth connection wires 23, 24 connected to both ends of the lower chain wound around the lower sprocket operate the front end of the insertion part to be bent horizontally in conjunction with the pair of the third and fourth operation wires 13, 14 disposed parallel to each other on the lower side inside the insertion part in the figure, the present disclosure is not limited thereto and the vertically and horizontally bending operation may be conversely performed according to the endoscope design.

In addition, although it has been illustrated and described that the rotations of the upper and lower sprockets are performed by the manual rotational operation of the worker gripping the upper and lower operation handles provided in the operation part, the rotations of the upper and lower sprockets are not limited thereto and may be performed by connecting a rotary shaft assembled with the upper and lower sprockets to a driving means such as a motor and using a separate remote operation means such as a joystick for controlling the driving means.

As illustrated in FIGS. 3, 4, 5, 6, and 7, the first detachable module 100 includes first and second rack gears 110, 120 arranged on the upper side thereof, third and fourth rack gears 130, 140 arranged on the lower side thereof, a first pinion gear 150 disposed between the first and second rack gears, a second pinion gear 160 disposed between the third and fourth rack gears, a gear shaft 170 coupled to the first and second pinion gears 150, 160, and a first module main body 180 for accommodating the first and second rack gears, the third and fourth rack gears, the first pinion gear, and the second pinion gear therein.

The first module main body 180 is a block structure having a substantially cuboid shape which has first, second, third, and fourth linear guide holes 181, 182, 183, 184 formed to penetrate the insides of the bodies in a longitudinal direction and a central placement hole 189, which communicates with the first, second, third, and fourth linear guide holes in a thickness direction substantially perpendicular to the longitudinal direction, formed to penetrate the center of the body.

Outer surfaces of both sides of the first module main body 180 are opened by having both ends of the first, second, third, and fourth linear guide holes 181, 182, 183, 184 exposed, respectively, and the upper and lower surfaces of the first module main body 180 are opened by having both ends of the central placement hole 189 exposed.

The first and second rack gears 110, 120 are linear bar-type gear members which are connected to the respective one ends of the first and second operation wires 11, 12 arranged parallel to each other on the upper side inside the insertion part, and have the respective other ends of the first and second operation wires detachably coupled to the second detachable module, and the third and fourth rack gears 130, 140 are linear bar-type gear members which are connected to the respective one ends of the third and fourth operation wires 13, 14 arranged parallel to each other on the lower side inside the insertion part, and have the respective other ends of the third and fourth operation wires detachably coupled to the second detachable module.

The first pinion gear 150 is a gear member which is gear-engaged between the first rack gear 110 and the second rack gear 120 disposed parallel to each other, and thus linearly moves the first and second rack gears in opposite directions so as to operate the front end of the insertion part to be bent vertically upon rotational operation of the upper operation handle.

The second pinion gear 160 is a gear member which is gear-engaged between the third rack gear 130 and the fourth rack gear 140 disposed parallel to each other just below the first and second rack gears, and thus linearly moves the third and fourth rack gears in opposite directions so as to operate the front end of the insertion part to be bent horizontally upon rotational operation of the lower operation handle.

The first, second, third, and fourth rack gears 110, 120, 130, 140 are slidably assembled in the first, second, third, and fourth linear guide holes, include linear bars 111, 121, 131, 141 having predetermined lengths having both ends externally exposed to both sides of the first module main body 180, and include linear gear teeth 112, 122, 132, 142 having predetermined lengths which are formed on the linear bar and gear-engaged with circular gear teeth formed on the outer circumferential surfaces of the first and second pinion gears 150, 160.

Although it has been illustrated and described that the linear gear teeth 112, 122, 132, 142 are integrally provided on the outer surfaces of the linear bars of the first and second rack gears facing the first pinion gear, and the outer surfaces of the linear bars of the third and fourth rack gears facing the second pinion gear, respectively, they are not limited thereto and may be provided in an assembling type.

The linear gear teeth 112, 122, 132, 142 are exposed through communication holes 112a, 122a, 132a, 142a cutout to communicate the first, second, third, and fourth linear guide holes with the central placement hole, such that the first and second rack gears and the first pinion gear, and the third and fourth rack gears and the second pinion gear are gear-engaged with each other.

The first, second, third, and fourth linear guide holes 181, 182, 183, 184 may be composed of guide holes 181a, 182a, 183a, 184a having a substantially circular shape which are guided by the contact between the outer circumferential surfaces of the respective linear bars of the first, second, third, and fourth rack gears 110, 120, 130, 140 and the inner surfaces thereof and extension holes 181b, 182b, 183b, 184b extending from the guide holes to the outside so that the respective gear teeth of the first, second, third, and fourth rack gears 110, 120, 130, 140 are guided and moved without interference.

At this time, although it has been illustrated and described that the outer circumferential surfaces of the respective linear bars of the first, second, third, and fourth rack gears 110, 120, 130, 140 and the inner circumferential surfaces of the respective guide holes of the first, second, third, and fourth linear guide holes are entirely in contact with each other, the present disclosure is not limited thereto and may have a linear-type protrusion having a predetermined length in a guide direction on the outer circumferential surface of the linear bar or the inner circumferential surface of the guide hole so as to smoothly perform the linear guide movement while reducing the frictional resistance therebetween by partially contacting the outer circumferential surfaces of the respective linear bars of the first, second, third, and fourth rack gears 110, 120, 130, 140 with the inner circumferential surfaces of the respective guide holes of the first, second, third, and fourth linear guide holes to reduce contact areas.

The outer surfaces of both sides of the first module main body 180 corresponding to the first, second, third, and fourth rack gears 110, 120, 130, 140 are cutout to form linear-type guide slits 185, 186, 187, 188 therein, and the respective linear bars of the first, second, third, and fourth rack gears 110, 120, 130, 140 include movable bodies 113, 123, 133, 143 moving along the linear-type guide slits.

The movable bodies 113, 123, 133, 143 are detachably assembled in assembling grooves recessed in the centers of the lengths of the liner bars 111, 121, 131, 141 by fastening members, and the linear gear tooth and the movable body are preferably provided on the outer surface of the linear bar with a phase difference of about 90 degrees.

In addition, the respective one ends of the first, second, third, and fourth rack gears 110, 120, 130, 140 corresponding to the first, second, third, and fourth operation wires 11, 12, 13, 14 are connected to the respect one ends of the first, second, third, and fourth operation wires via a first buffer part 410 having a first buffer body integrally connected thereto.

The respective other ends of the first, second, third, and fourth rack gears 110, 120, 130, 140 corresponding to the second detachable module 200 have first, second, third, and fourth connecting ports 115, 125, 135, 145 locked and connected to first, second, third, and fourth connected ports 215, 225, 235, 245 provided on the respective ends of the first, second, third, and fourth connection shafts 210, 220, 230, 240 provided in the second detachable module 200.

Here, it is possible to transfer powers selectively reciprocating the first, second, third, and fourth operation wires so as to operate the front end of the insertion part to be bent vertically and horizontally upon rotational operation by the upper and lower operation handles provided in the operation part by the locking-connection between the first, second, third, and fourth connecting ports 115, 125, 135, 145 of the first, second, third, and fourth rack gears 110, 120, 130, 140 and the first, second, third, and fourth connected ports 215, 225, 235, 245 of the first, second, third, and fourth connection shaft 210, 220, 230, 240.

The gear shaft 170 is a shaft member in which the first and second pinion gears 150, 160 gear-engaged with the first, second, third, and fourth rack gears 110, 120, 130, 140 are rotatably assembled with vertically predetermined intervals and correspondingly inserted into and fixedly installed to the central placement hole 189 of the first module main body.

The lower end of the gear shaft 170 is integrally provided with a plate bracket 173 assembled by a fastening member by contacting the outer surface of the first module main body while covering one end of the opening end of the central placement hole 189, and the upper end of the gear shaft is provided with a separation prevention clip 156 for preventing the first and second pinion gears from being separated to the outside.

A first cylindrical sleeve 155 is provided between the first pinion gear 150 and the separation prevention clip 156 to maintain the interval therebetween, and a second cylindrical sleeve 165 is also provided between the first pinion gear 150 and the second pinion gear 160 to maintain the interval therebetween.

The outer surfaces of the gear shaft 170 corresponding to the first and second pinion gears 150, 160 have first and second ring-type grooves recessed, respectively, and the first and second ring-type grooves are provided with first and second elastic rings 171, 172 made of a rubber material so that the inner circumferential surfaces and outer circumferential surfaces of the first and second pinion gears 150, 160 are elastically in contact with each other.

It is possible to reduce the occurrence of noise due to backlash caused by gear-engaging between the first and second rack gears 110, 120 and the first pinion gear 150, and between the third and fourth rack gears 130, 140 and the second pinion gear 160 by the elastic contact between the respective inner circumferential surface of the first and second pinion gears 150, 160 and the outer circumferential surfaces of the first and second elastic rings 171, 172, and to move the first and second rack gears linearly and more smoothly in opposite directions without using a lubricant and move the third and fourth rack gears linearly and more smoothly in opposite directions without using the lubricant when operating the front end of the insertion part to be bent vertically and horizontally.

Figure 4:
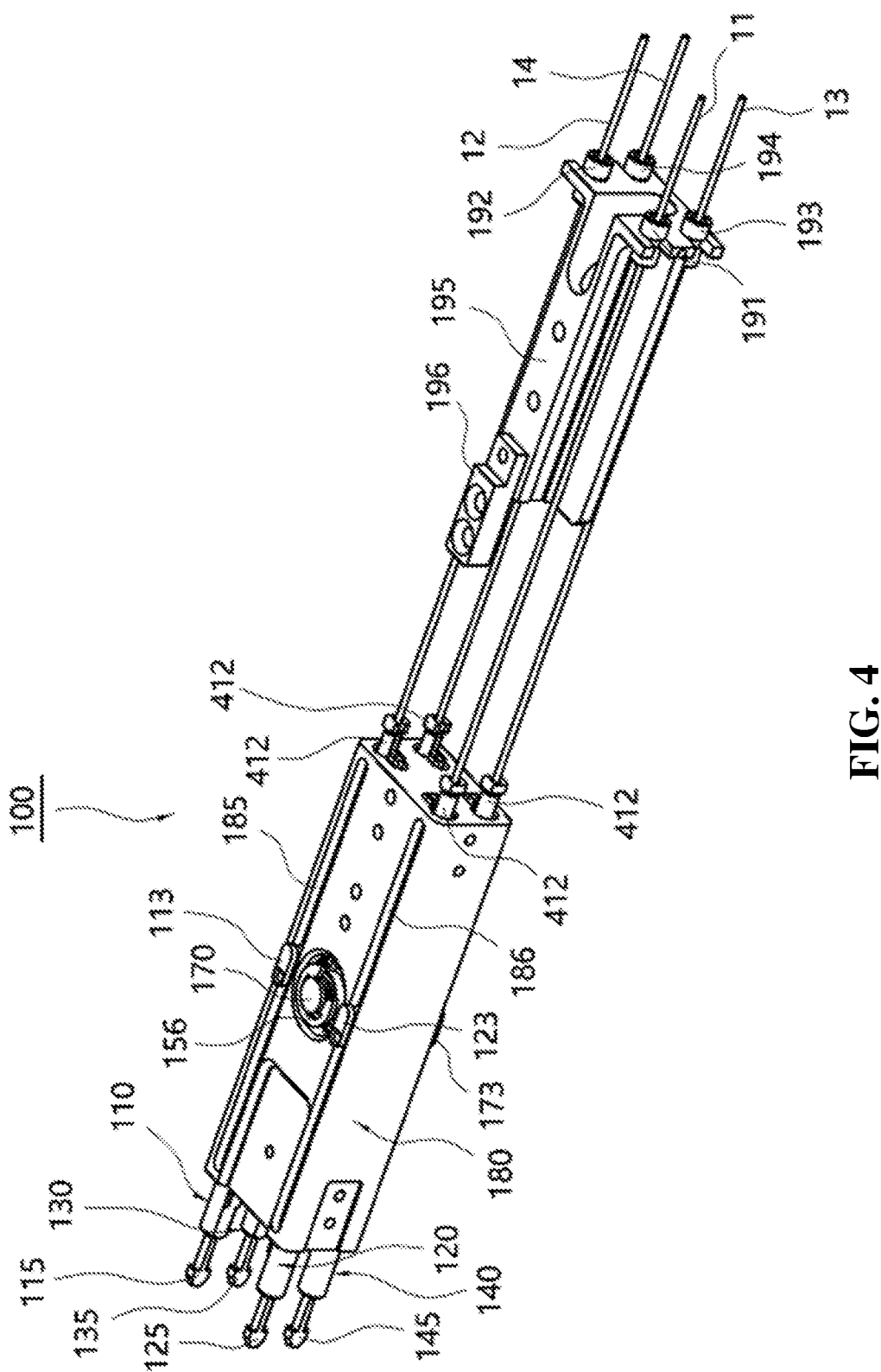
FIG. 4 is a perspective diagram illustrating a first detachable module of the detachable unit provided in the detachable endoscope having the wire buffer function according to the exemplary embodiment of the present disclosure.
Figure 5:
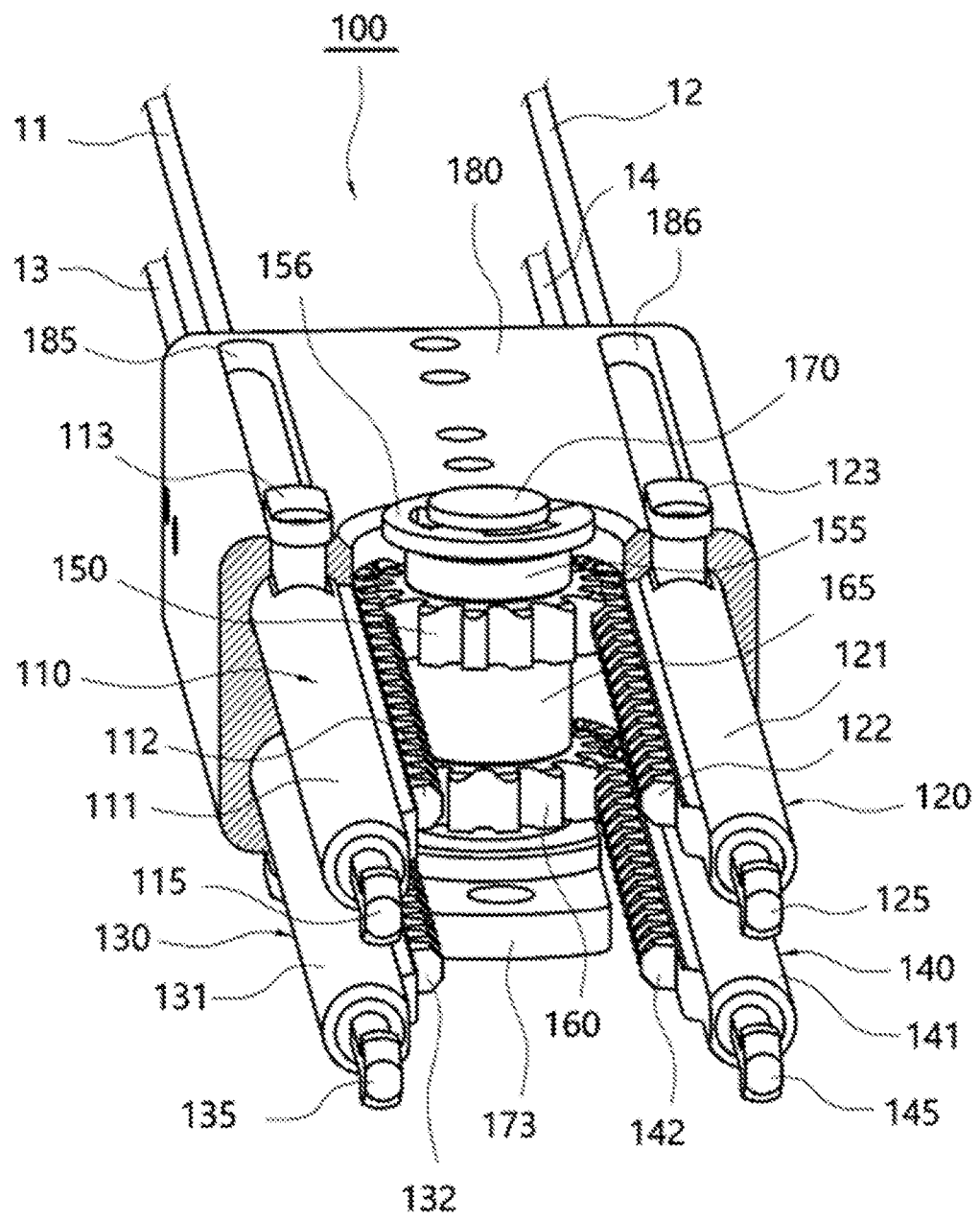
FIG. 5 is a cross-sectional perspective diagram illustrating the first detachable module of the detachable unit provided in the detachable endoscope having the wire buffer function according to the exemplary embodiment of the present disclosure.
Figure 6:
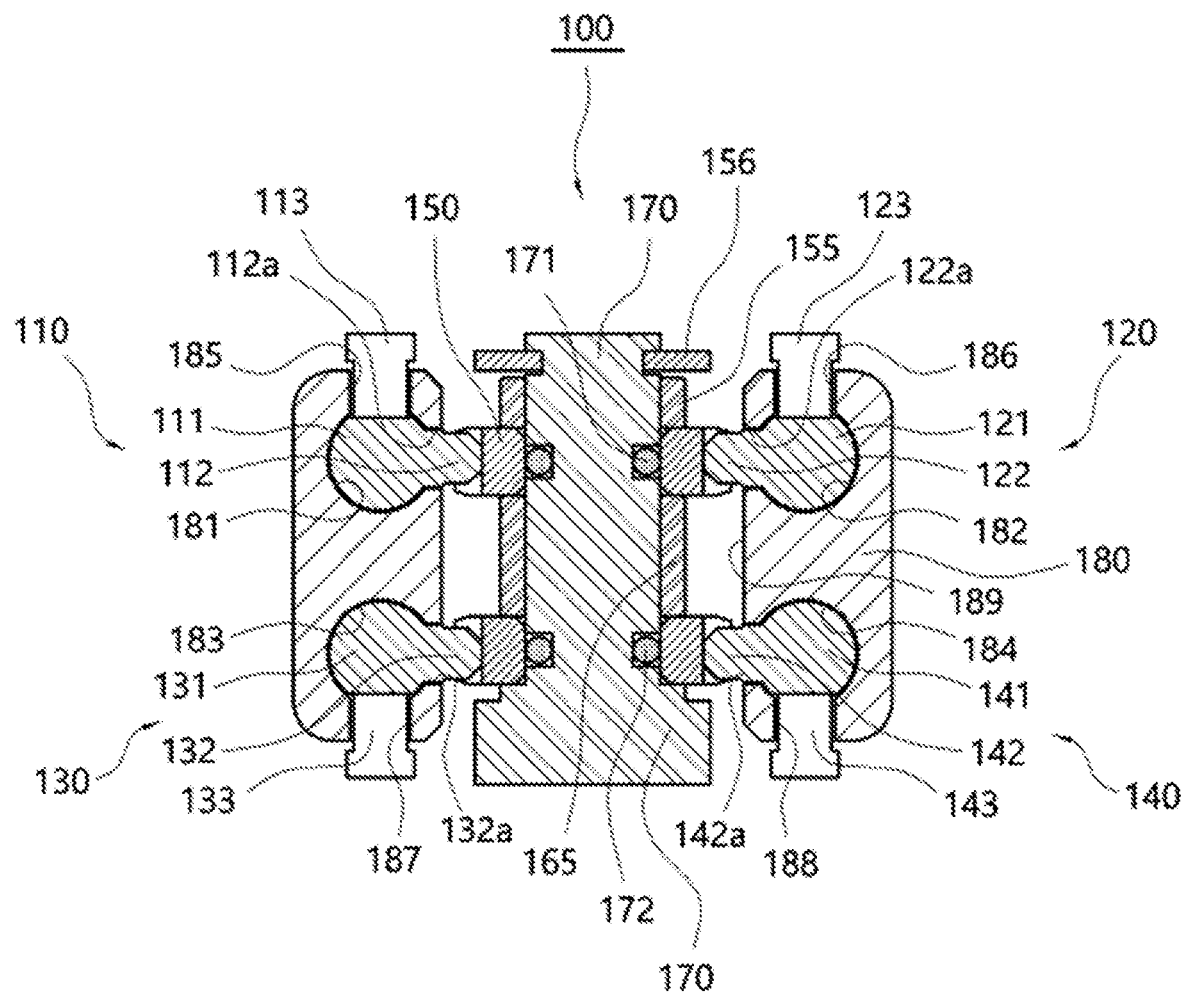
FIG. 6 is a longitudinal cross-sectional diagram illustrating the first detachable module of the detachable unit provided in the detachable endoscope having the wire buffer function according to the exemplary embodiment of the present disclosure.
Figure 7:
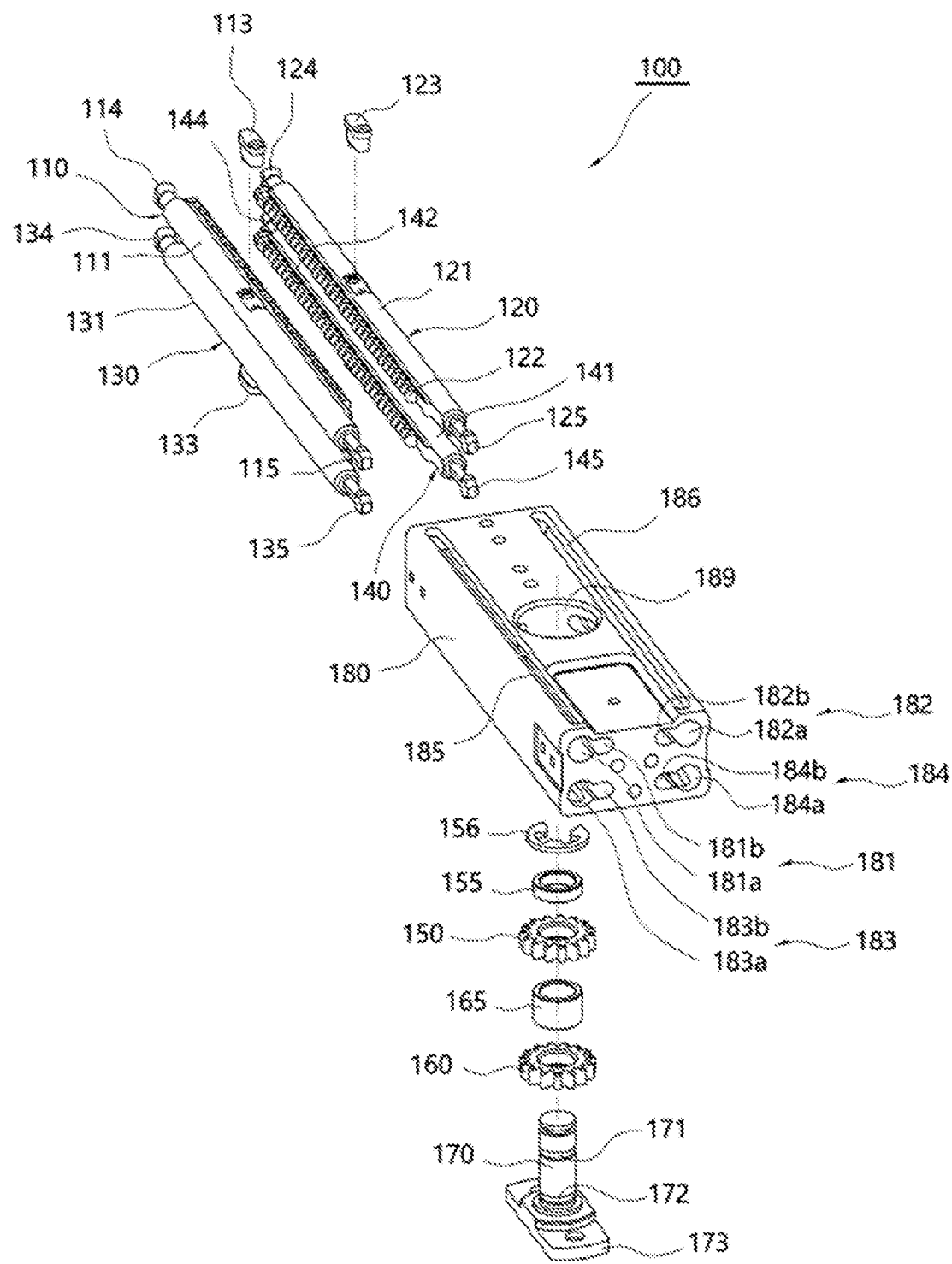
FIG. 7 is an exploded perspective diagram illustrating the first detachable module of the detachable unit provided in the detachable endoscope having the wire buffer function according to the exemplary embodiment of the present disclosure.

In addition, as illustrated in FIG. 4, the first detachable module 100 includes a wire support part 190 for supporting the linear movements of the first, second, third, and fourth operation wires 11, 12, 13, 14 coupled to one ends of the first, second, third, and fourth rack gears.

The wire support part 190 has first, second, third, and fourth support bodies 191, 192, 193, 194 having support holes, into which the first, second, third, and fourth operation wires 11, 12, 13, 14 are correspondingly inserted, formed to penetrate the insides thereof, a support block 195 for fixedly installing the first, second, third, and fourth support bodies on one end thereof, and a connection bracket 196 for detachably assembling the support block 195 to one end of the first module main body 180 by a plurality of fastening members.

The first, second, third, and fourth support bodies 191, 192, 193, 194 have the support holes formed to penetrate the centers of the bodies, are formed of cylindrical members having annular grooves recessed in the outer surfaces thereof, and one end of the support block 195 has a plurality of fitting and fixing pieces, into which the grooves formed on the respective outer surfaces of the first, second, third, and fourth support bodies are correspondingly inserted and fixed.

The first detachable module 100 having the above configuration has the respective front ends of the first, second, third, and fourth connecting ports corresponding to the second detachable module of the operation part located on the same vertical surface in an initial standby state where the first and second pinion gears 150, 160 are located on the centers of the lengths of the first, second, third, and fourth rack gears 110, 120, 130, 140.

In this state, when the first detachable module provided on the rear end of the insertion part and the second detachable module provided on the front end of the operation part are coupled to each other, the first, second, third, and fourth connecting ports 115, 125, 135, 145 provided in the first, second, third, and fourth rack gears 110, 120, 130, 140 of the first detachable module and the first, second, third, and fourth connected ports 215, 225, 235, 245 of the first, second, third, and fourth connection shafts 210, 220, 230, 240 of the second detachable module 200 are locked and connected to each other.

In addition, in the state where the first, second, third, and fourth connecting ports 115, 125, 135, 145 and the first, second, third, and fourth connected ports 215, 225, 235, 245 are locked and connected to each other, when the first rack gear is moved by a predetermined distance in the left direction in the figure by the forward rotation of the upper operation handle 28 provided in the operation part, the second rack gear may be linearly moved by the same predetermined distance in the right direction, which is the opposite direction, to quantitatively pull and move the first operation wire and to quantitatively push and move the second operation wire by the gear-engagement between the first and second rack gears and the first pinion gear, thereby operating the front end of the insertion part to be bent upward at a predetermined angle in proportion to the forward rotation amount of the upper operation handle 28.

Conversely, when the second rack gear is moved by a predetermined distance in the left direction in the figure by the reverse rotation of the upper operation handle 28, the first rack gear may be linearly moved by the same predetermined distance in the right direction, which is the opposite direction, to quantitatively pull and move the second operation wire and to quantitatively push and move the first operation wire by the gear-engagement between the first and second rack gears and the first pinion gear, thereby operating the front end of the insertion part to be bent downward at a predetermined angle in proportion to the reverse rotation amount of the upper operation handle 28.

In addition, the operation of operating the front end of the insertion part to be bent horizontally at a predetermined angle by linearly moving the third and fourth rack gears by predetermined distances in opposite directions by the forward or reverse rotation of the lower operation handle 29 provided in the operation part to pull and move or push and move the third and fourth operation wires in opposite directions is the same as the linear movements of the first and second rack gears, so that a description thereof will be omitted.

Therefore, the endoscopic surgery may be performed, which removes or cures a lesion site by the treatment tool entering into the insertion part while illuminating, photographing, and confirming the lesion site in the body by operating the front end of the insertion part inserted into the body to be bent vertically and horizontally by the selective rotational operations of the upper and lower operation handles provided in the operation part upon endoscopic surgery.

Figure 8A:
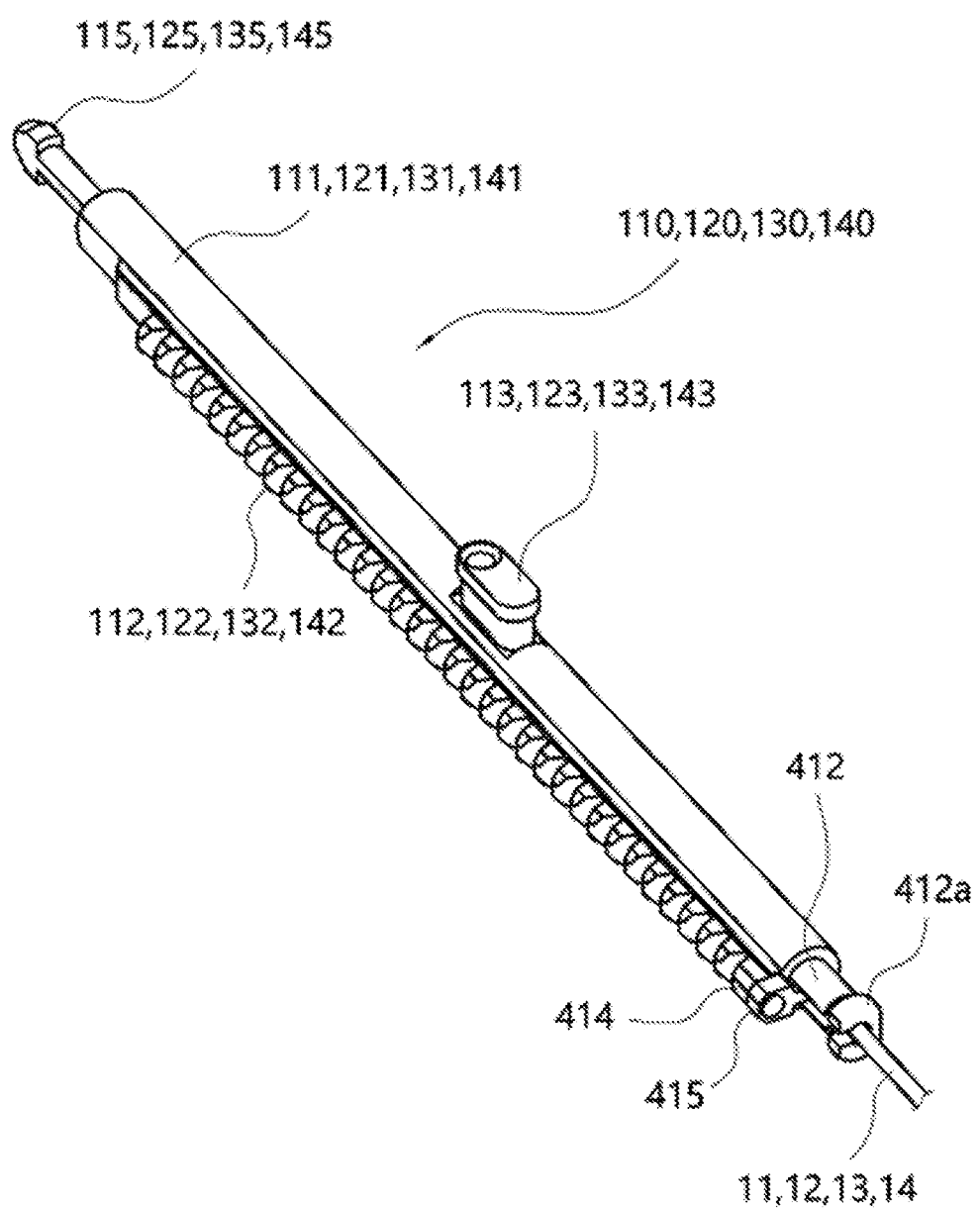
FIGS. 8A, 8B, and 8C are an assembling diagram, an exploded perspective diagram, and a cross-sectional diagram illustrating a first buffer part provided in the detachable endoscope having the wire buffer function according to the exemplary embodiment of the present disclosure.
Figure 8B:
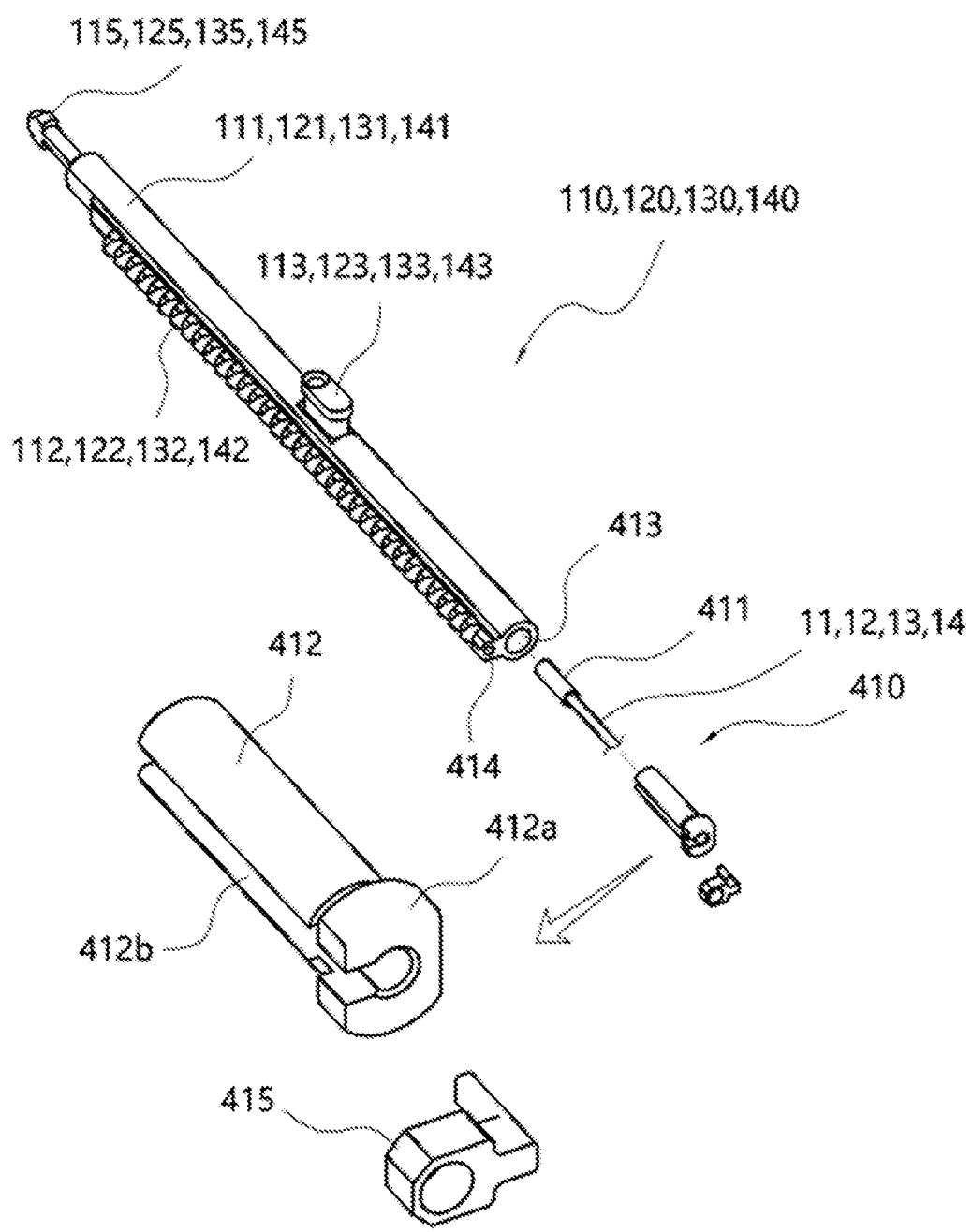
Figure 8C:
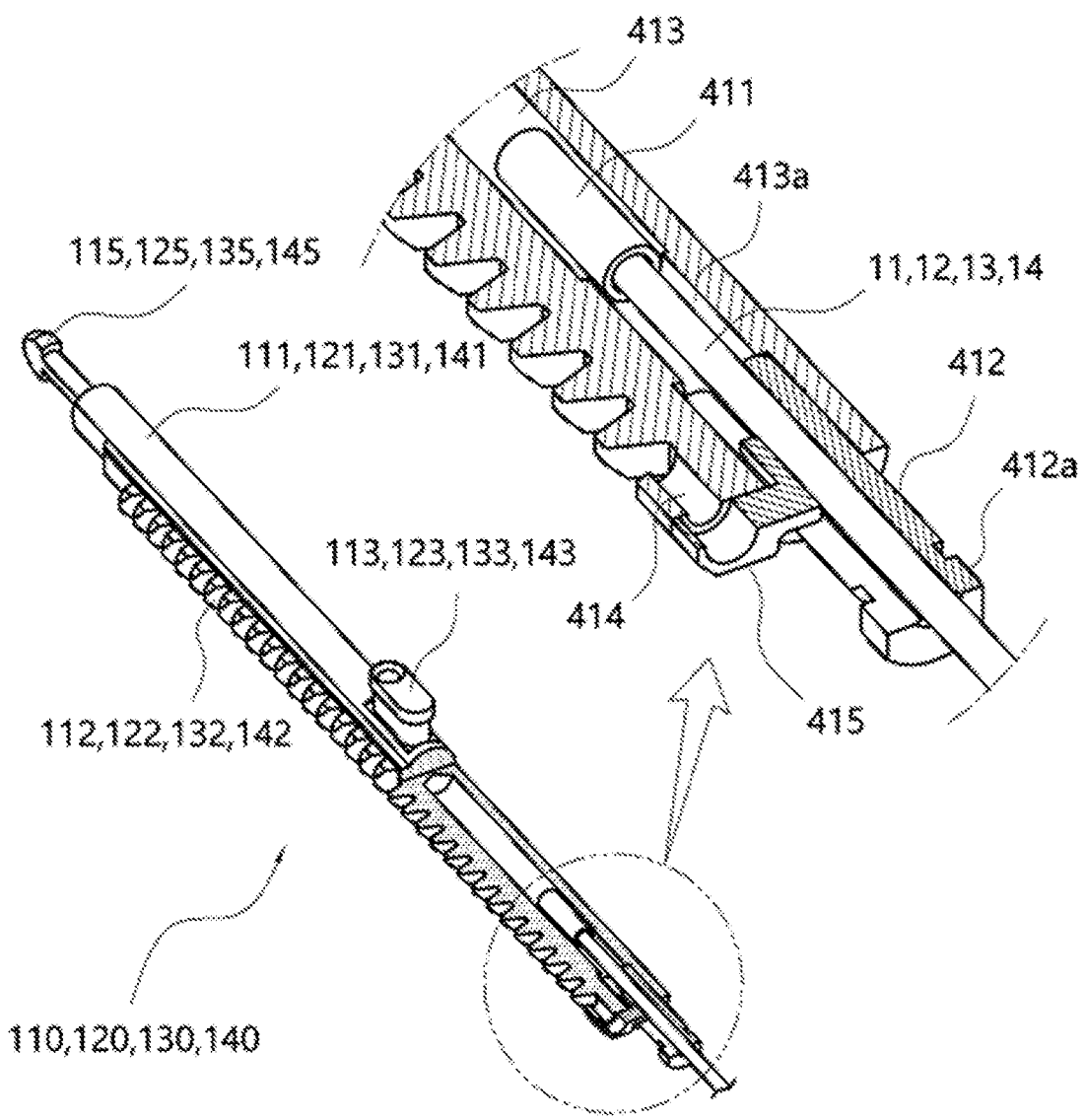

As illustrated in FIGS. 8A, 8B, and 8C, the first buffer part 410 gives buffer functions to portions connecting the first, second, third, and fourth operation wires 11, 12, 13, 14 provided inside the insertion part 10 to the first, second, third, and fourth rack gears 110, 120, 130, 140 provided in the first detachable module 100.

The first buffer parts 410 include the first buffer bodies 411 having substantially cylindrical shapes integrally provided on the ends, which are the respective rear ends of the first, second, third, and fourth operation wires 11, 12, 13, 14, and form first buffer lines holes 413 having predetermined lengths, which are formed to be opened to the outside, inside the respective one ends of the linear bars 111, 121, 131, 141 of the first, second, third, and fourth rack gears 110, 120, 130, 140.

Therefore, the first buffer bodies 411 entering into the opened end of the first buffer line holes 413 having one end closed and disposed therein are moved inside the first buffer line holes in conjunction with the movements of the first, second, third, and fourth operation wires 11, 12, 13, 14.

The opened ends of the respective first buffer line holes formed to be opened to the outside on one ends of the first, second, third, and fourth rack gears 110, 120, 130, 140 have first buffer stoppers 412 having hollow cylindrical shapes correspondingly inserted and fixedly installed therein, in which the first buffer stoppers have inner holes formed in the bodies so that the operation wires having the first buffer bodies 411 pass through the inner holes freely in order to prevent the first buffer bodies from being separated to the outside.

At this time, the first buffer stopper 412 is preferably formed of a hollow cylindrical body which has a slit with a reducing outer diameter cutout on the outer surface thereof in the longitudinal direction so as to have an elastic force when entering into the first buffer line hole.

The outer ends of the first buffer stoppers 412 are preferably provided with protrusions 412a having planar portions exposed to the ends of the first, second, third, and fourth rack gears so as to facilitate the work of separating the first buffer stoppers assembled inside the first buffer line holes to the outside.

The outer surfaces of the first buffer stoppers 412 are provided with fixing parts 415 having assembling holes having fastening members fastened to fastening holes 414 formed in the respective ends of the first, second, third, and fourth rack gears 110, 120, 130, 140 disposed to penetrate the insides thereof.

The inner surface of the opened end of the first buffer line hole 413 is provided with an annular first inner projection 413a formed to protrude therefrom so as to form a circular hole through which the first buffer body 411 may pass while preventing an excessive internal entry by contacting the end of the first buffer stopper.

Therefore, the first buffer bodies provided on the respective ends of the first, second, third, and fourth operation wires penetrating the inner holes of the first buffer stoppers are reciprocatably inserted into and disposed in the first buffer line holes formed in the respective ends of the first, second, third, and fourth rack gears, and the first buffer stoppers inserted into the opened ends of the first buffer line holes are fixedly installed by the fastening members fastened to the fastening holes formed in the respective ends of the first, second, third, and fourth rack gears through the assembling holes of the fixing parts, so that the first buffer bodies are linearly moved without locking in conjunction with any one of the first, second, third, and fourth operation wires in the buffer sections of the first buffer line holes without being separated to the outside by the locking with the front ends of the first buffer stoppers or generate locking forces by contacting the first buffer stoppers.

It is possible to compensate the length errors of the first, second, third, and fourth operation wires due to the inner and outer curved portions of the curved deformation portions generated in the middle portion of the length of the insertion part upon storing or handling the insertion part 10 completely separated from the operation part 20 by the first buffer part 410 having the above configuration, thereby constantly maintaining the aligned locations of the first, second, third, and fourth connecting ports provided on the ends of the first, second, third, and fourth rack gears and located on the end of the first detachable module with predetermined intervals at all times.

That is, the first and second pinion gears 150, 160 provided in the first module main body of the first detachable module is gear-engaged with the centers of the lengths of the first, second, third, and fourth rack gears 110, 120, 130, 140, and the first buffer body 141 provided on the respective ends of the first, second, third, and fourth operation wires are located on the middle portions of the lengths of the first buffer line holes provided on the respective ends of the first, second, third, and fourth rack gears 110, 120, 130, 140.

Figure 9A:
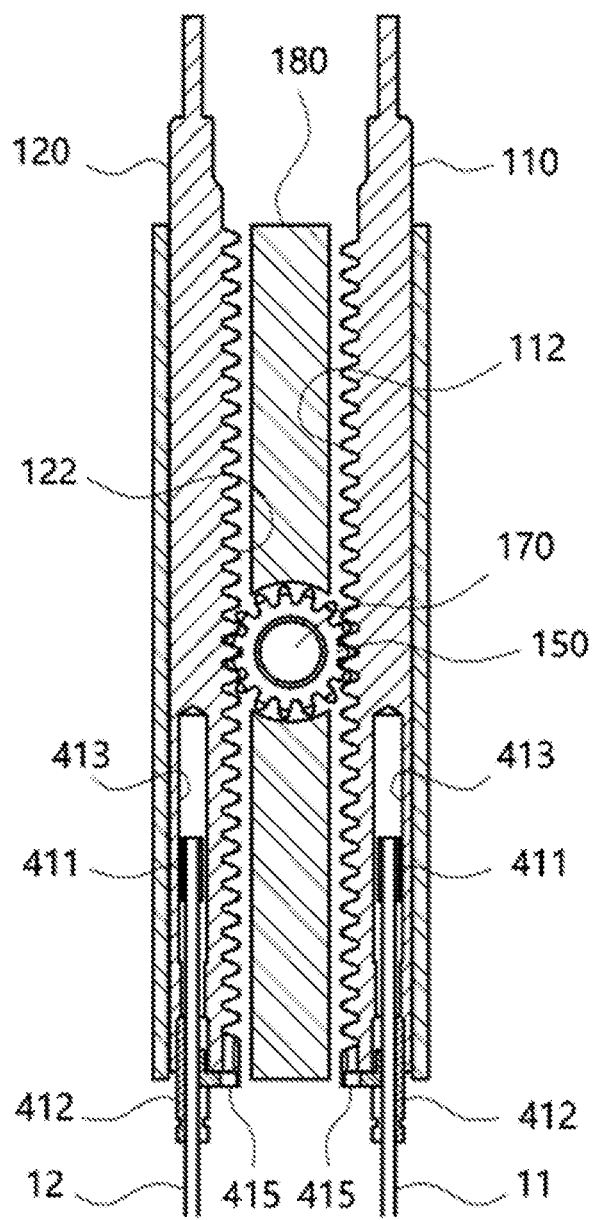
FIGS. 9A, 9B, and 9C are diagrams illustrating operation states between the first detachable module and a first buffer part provided in the detachable endoscope having the wire buffer function according to the exemplary embodiment of the present disclosure.

In the initial separation state of the insertion part, if the operation wire close to the outer curved portion among the first, second, third, and fourth operation wires is forcibly moved toward the front end of the insertion part while the curved deformation portion of the middle portion of the length of the insertion part separated from the operation part 20 is generated, as illustrated in FIG. 9A, the first buffer body 141 provided on the end of the forcibly moved operation wire is moved in location together with the operation wire without locking with the rack gear in the middle portion of the length of the first buffer line hole 413 by the length error of the operation wire caused by the curved deformation portion, so that the first, second, third, and fourth rack gears having the first, second, third, and fourth connecting ports may be aligned and located at the same locations of the end of the first module main body at all times while maintaining the initial standby states.

In addition, the respective front ends of the first, second, third, and fourth connecting ports having one-one correspondence with the first, second, third, and fourth connected ports provided in the second detachable module of the operation part may be located on the same vertical surface of the end of the first detachable module, thereby performing the work of connecting the first, second, third, and fourth connected ports provided in the second detachable module and the first, second, third, and fourth connecting ports of the first detachable module upon working of coupling the insertion part and the operation part, which are separated from each other, without connection failure.

Figure 9B:
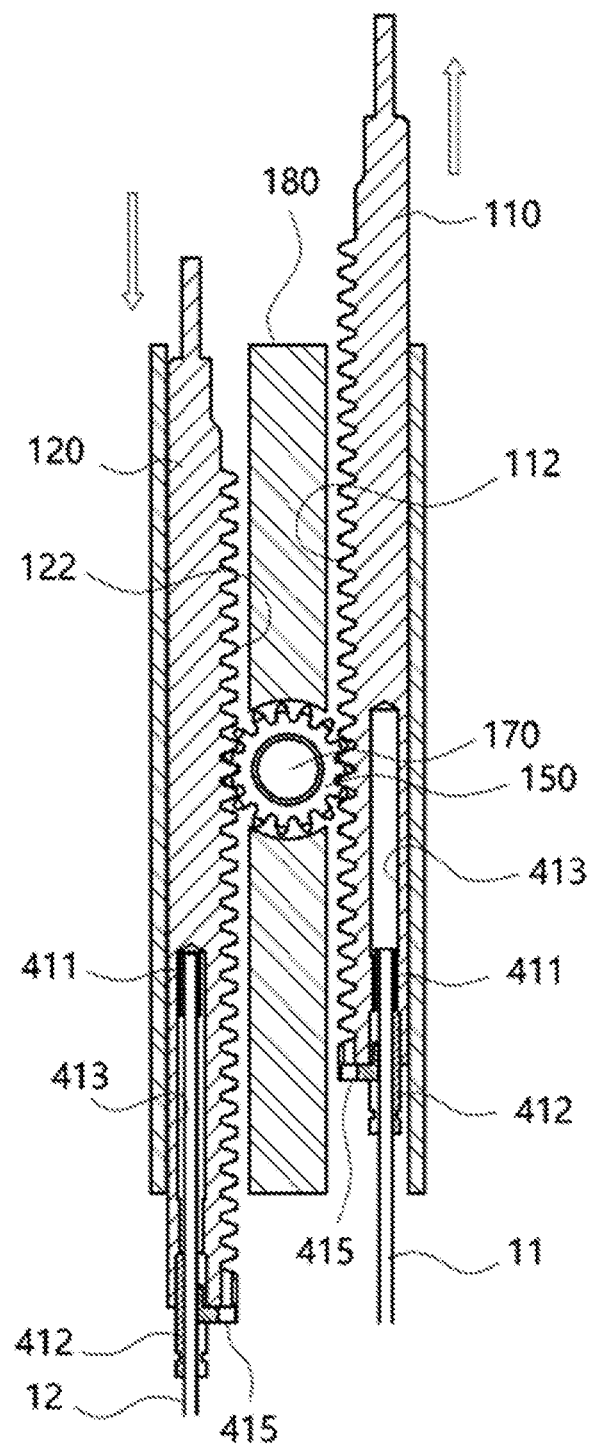
Figure 9C:
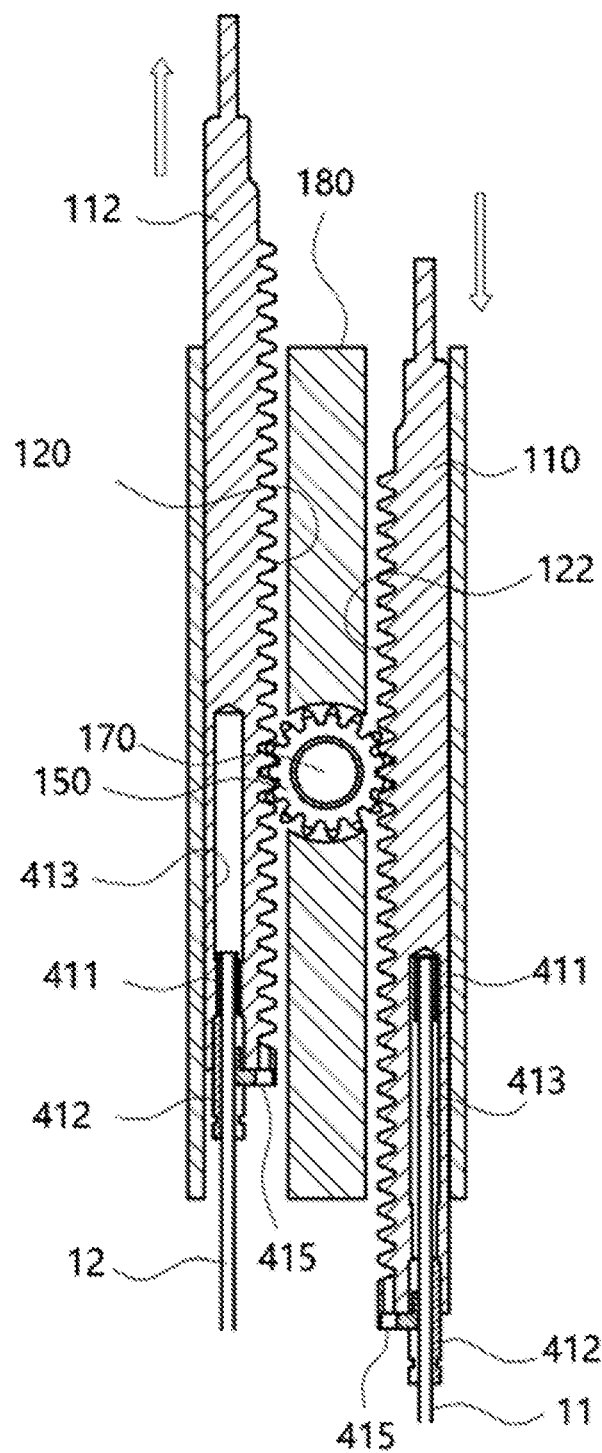
Figure 10:
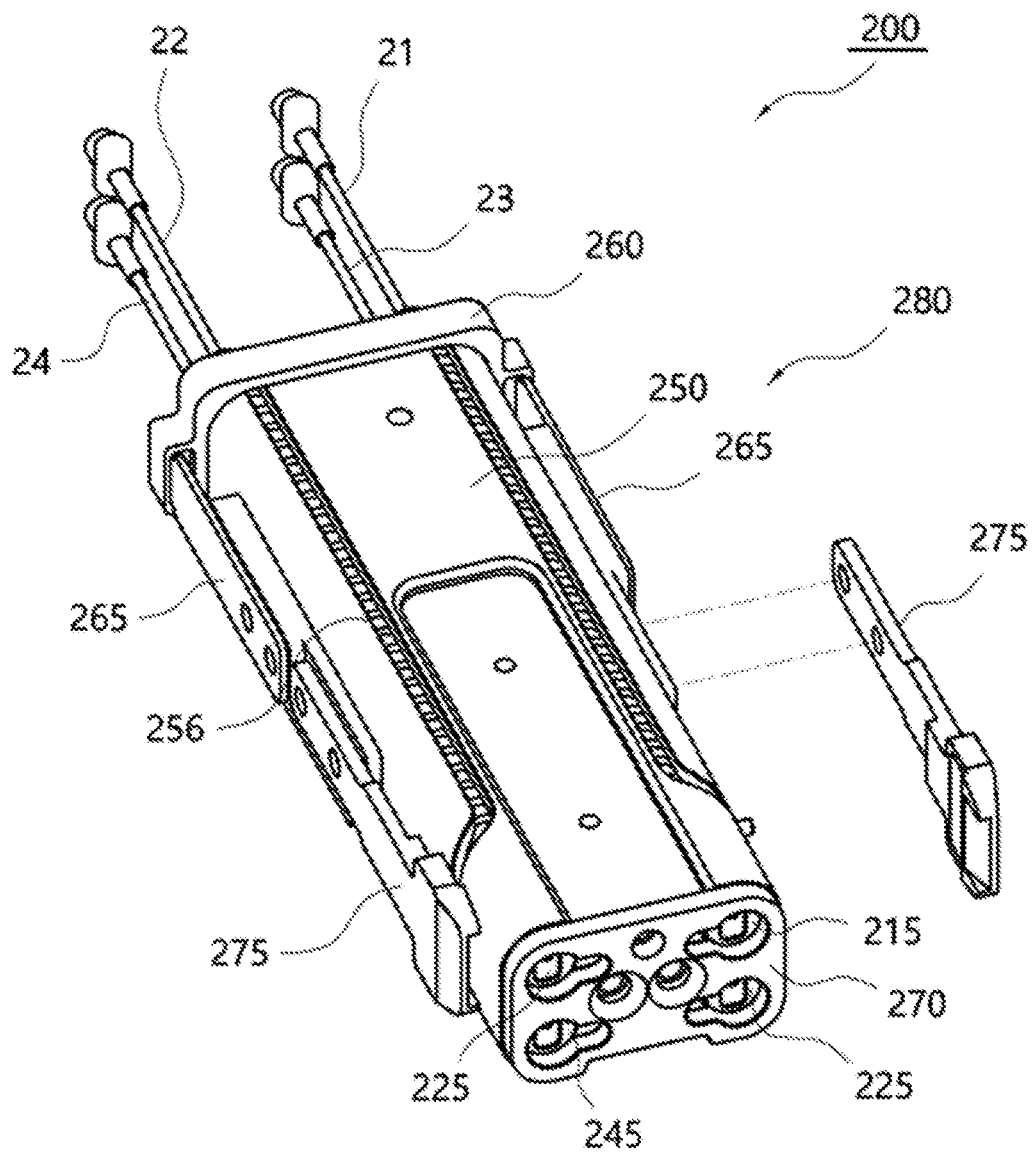
FIG. 10 is a perspective diagram illustrating a second detachable module of the detachable unit provided in the detachable endoscope having the wire buffer function according to the exemplary embodiment of the present disclosure.
Figure 11:
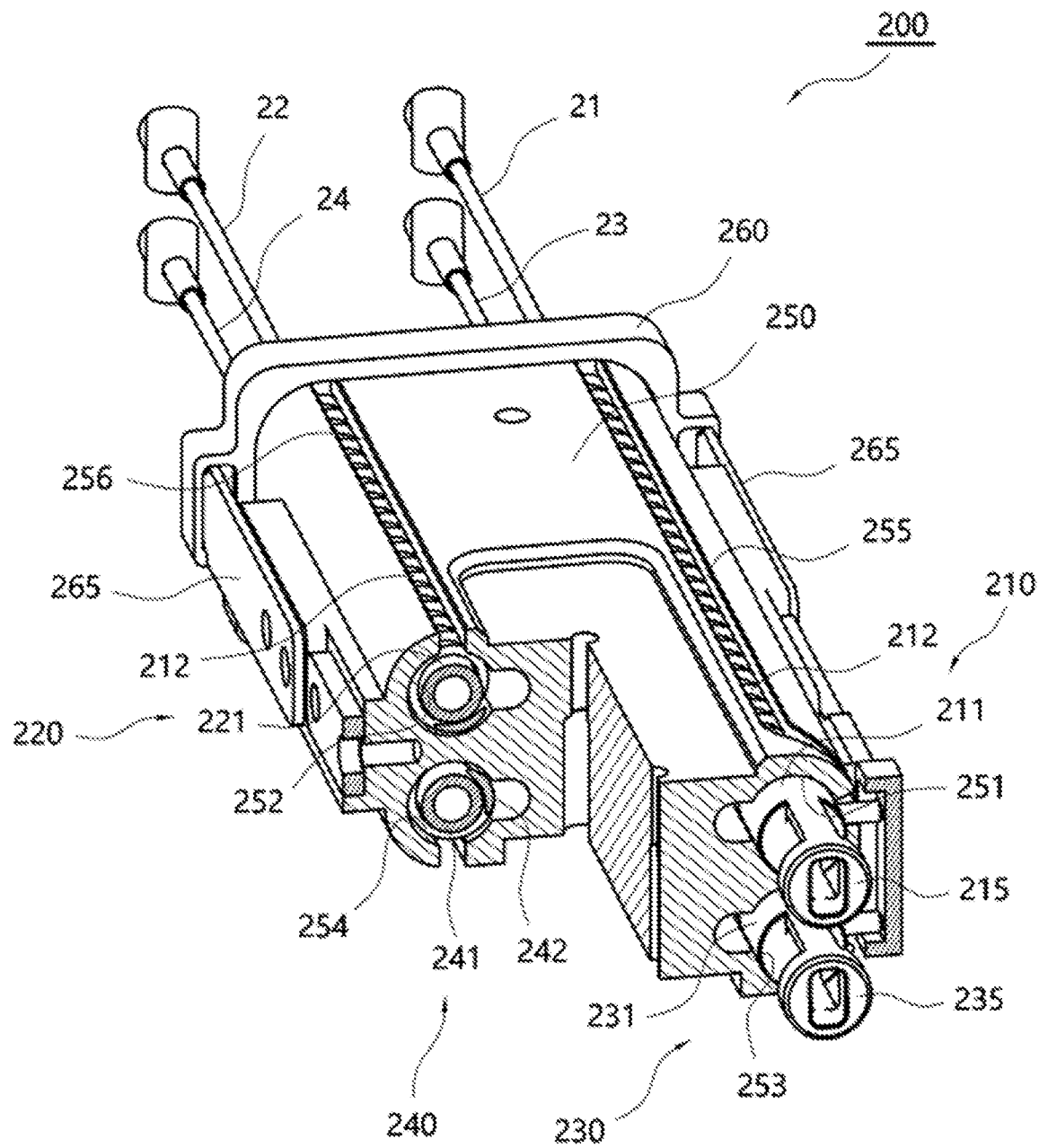
FIG. 11 is a cross-sectional perspective diagram illustrating the second detachable module of the detachable unit provided in the detachable endoscope having the wire buffer function according to the exemplary embodiment of the present disclosure.
Figure 12:
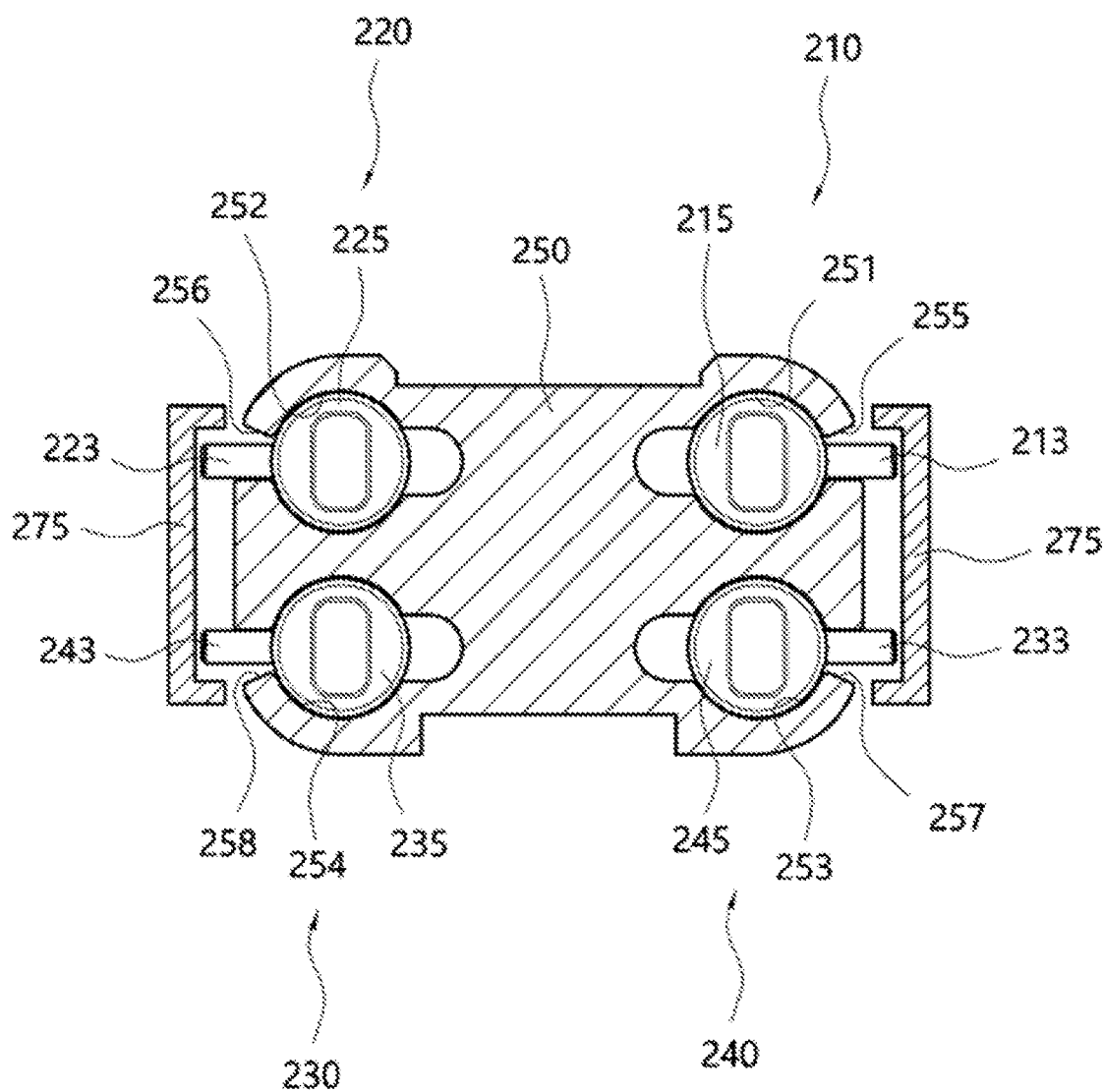
FIG. 12 is a longitudinal cross-sectional diagram illustrating the second detachable module of the detachable unit provided in the detachable endoscope having the wire buffer function according to the exemplary embodiment of the present disclosure.
Figure 13:
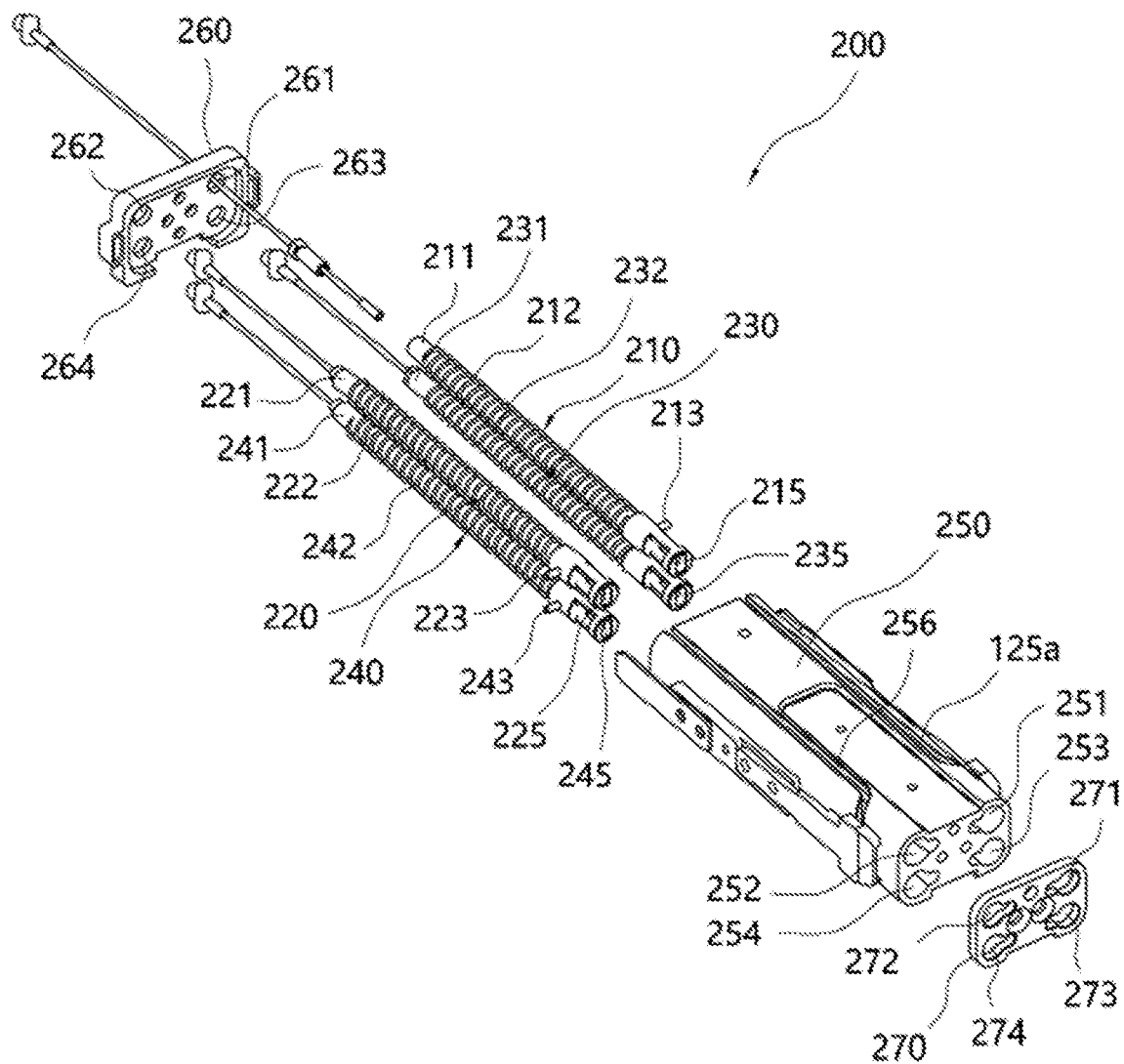
FIG. 13 is an exploded perspective diagram illustrating the second detachable module of the detachable unit provided in the detachable endoscope having the wire buffer function according to the exemplary embodiment of the present disclosure.

Meanwhile, in a state where the first, second, third, and fourth connected ports provided in the second detachable module and the first, second, third, and fourth connecting ports of the first detachable module are connected to each other and the insertion part and the operation part are coupled to each other, as illustrated in FIGS. 9B and 9C, in order to operate the front end of the insertion part to be bent vertically or horizontally, when the first and fourth rack gears of any one among the first, second, third, and fourth rack gears are pulled toward the operation part by the selective rotation of the operation part to move by predetermined distances, the first buffer bodies disposed in the first buffer line holes formed in the ends of the pulled and moved first and fourth rack gears generate the locking forces while contacting the ends of the first buffer stoppers, thereby performing the consecutive pulling movements of the first and fourth rack gears.

In addition, the first and fourth rack gears and the remaining second and third rack gears are quantitatively moved in opposite directions and perform the vertically and horizontally bending operation for the front end of the insertion part by the gear-engagement between the first and second pinion gears and the first, second, third, and fourth rack gears.

Meanwhile, as illustrated in FIGS. 10, 11, 12, and 13, the second detachable module 200 includes first and second connection shafts 210, 220 arranged parallel to each other on the upper side thereof to be interlocked with the first and second operation wires, third and fourth connection shafts 230, 240 arranged parallel to each other on the lower side thereof, and a second module main body 280 for accommodating the first, second, third, and fourth connection shafts therein.

The second module main body 280 includes a main body block 250 having a substantially cuboid shape, in which has first, second, third, and fourth linear through holes 251, 252, 253, 254 formed to penetrate the insides of the bodies in the longitudinal direction.

One end of the main body block 250 corresponding to the first, second, third, and fourth connection wires 21, 22, 23, 24 includes a first cover plate 260 having a plurality of first entry and exit holes 261, 262, 263, 264, through which the respective one ends of the first, second, third, and fourth connection shafts 210, 220, 230, 240 enter and exit, formed to penetrate the insides thereof.

The other end of the main body block 250 corresponding to the first detachable module 100 includes a second cover plate 270 having a plurality of second entry and exit holes 271, 272, 273, 274, through which the first, second, third, and fourth connecting ports 115, 125, 135, 145 of the first detachable module 100 enter and exit without interference, and to which the ends of the first, second, third, and fourth linear though holes correspond, formed to penetrate the insides thereof.

Here, the first cover plate 260 may be assembled and fixedly installed on one end of the main body block 250 by a first fixing bracket 265 provided on both sides of one end of the main body block 250, and the second cover plate 270 may be assembled and fixedly installed on the other end of the main body block 250 by a second fixing bracket 275 provided on both sides of the other end of the main body block 250.

The first, second, third, and fourth connected ports 215, 225, 235, 245 of the first, second, third, and fourth connection shafts 210, 220, 230, 240 are exposed to the outside through the plurality of second entry and exit holes formed on the second cover plate to penetrate the insides thereof.

The first and second connection shafts 210, 220 are linear-type shaft members in which the first and second connection wires 21, 22 arranged parallel to each other on the upper side inside the operation part and the respective one ends thereof are connected via a second buffer part 420, and the first and second connecting ports 115, 125 provided on the first and second rack gears of the first detachable module 100 and the respective other ends thereof are selectively locked and connected, and the third and fourth connection shafts 230, 240 are linear-type shaft members in which the third and fourth connection wires 23, 24 arranged parallel to each other on the lower side inside the operation part and the respective one ends thereof are connected via the second buffer part 420, and the third and fourth connecting ports 135, 145 provided on the third and fourth rack gears of the first detachable module and the respective other ends thereof are selectively locked and connected.

That is, the respective one ends of the first, second, third, and fourth connection shafts 210, 220, 230, 240 are connected to the respective one ends of the first, second, third, and fourth connection wires 21, 22, 23, 24 via the second buffer part 420 having the second buffer body integrally connected thereto.

The first, second, third, and fourth connection shafts 210, 220, 230, 240 have elastic bodies 212, 222, 232, 242 such as a coil spring and include operation bars 211, 221, 231, 241 which have substantially circular cross sections reciprocatably inserted into and disposed in the first, second, third, and fourth linear through holes 251, 252, 253, 254 formed in the main body block of the second module main body to penetrate the insides thereof, respectively, include guide pins 213, 223, 233, 243 provided on one ends of the operation bars corresponding to the first detachable module so as to rotationally displace the operation bars while being curvedly guided and moved along composite guide slits 255, 256, 257, 258 formed to be cutout on both side surfaces of the main body block 250 of the second module main body 280, and include the first, second, third, and fourth connected ports 215, 225, 235, 245 formed on one ends of the operation bars in which the guide pins are provided and selectively locked and connected to the first, second, third, and fourth connecting ports 115, 125, 135, 145 provided on the first, second, third, and fourth rack gears.

At this time, the inner diameter sizes of the first, second, third, and fourth linear through holes 251, 252, 253, 254 formed in the main body block to penetrate the insides thereof are preferably formed relatively larger than the overall outer diameters of the operation bars having the elastic bodies inserted into and disposed in the outside thereof.

The guide pins 213, 223, 233, 243 preferably have the outer diameters relatively larger size than the outer diameters of the operation bars and are provided in large diameter portions contacting the inner circumferential surfaces of the first, second, third, and fourth linear through holes 251, 252, 253, 254.

One ends of the elastic bodies 212, 222, 232, 242 provided on the operation bars are supported by contacting the first cover plate 260 assembled on one end of the main body block, and the other ends of the elastic bodies are supported by contacting the large diameter portions of the operation bars in which the guide pins 213, 223, 233, 243 are provided.

Therefore, in the process in which the first, second, third, and fourth connection shafts reciprocate inside the first, second, third, and fourth linear through holes 251, 252, 253, 254 formed in the main body block to penetrate the insides thereof, when an interval between the inner surface of the first cover plate and the large diameter portion of the operation bar is narrowed, the elastic bodies 212, 222, 232, 242 provided on the operation bars are compressed and deformed to generate elastic restoring forces for restoring the operation bars to the original locations thereof.

The first, second, third, and fourth linear through holes 251, 252, 253, 254 may be composed of guide holes having a substantially circular shape so that the interference between the first, second, third, and fourth rack gears composed of linear bars and gear teeth does not occur, and extension holes extending from the guide holes to the outside.

The first and second entry and exit holes of each of the first and second cover plate 260, 270 assembled on both ends of the main body block 250, respectively are also formed of circular guide holes and extension holes extending therefrom to penetrate the insides of the first and second cover plates.

The first, second, third, and fourth connected ports 215, 225, 235, 245 include slot-type locking holes exposing inner cavity portions formed in the respective ends of the first, second, third, and fourth connection shafts adjacent to the guide pins toward the first, second, third, and fourth connecting ports of the first detachable module, and the first, second, third, and fourth connecting ports 115, 125, 135, 145 include locking pieces which extend from the ends of the first, second, third, and fourth rack gears by predetermined lengths and have the front ends spread to both sides thereof.

In addition, the guide pins 213, 223, 233, 243 provided adjacent to the first, second, third, and fourth connected ports on the respective ends of the first, second, third, and fourth connection shafts are assembled to be guided and moved along the composite guide slits 255, 256, 257, 258 formed to be cutout on the outer surfaces of both sides of the main body block of the second module main body 280, and the composite guide slit has a curved section composed of a curved slit curvedly extending from the both side surfaces of the main body block to the upper and lower surfaces, and a linear section composed of a linear slit linearly extending from the upper and lower surfaces of the main body block.

Therefore, in the process in which the guide pins provided on the respective operation bars of the first, second, third, and fourth connection shafts are curvedly moved along the curved slits in the curved section by an external force, the operation bars of the first, second, third, and fourth connection shafts are rotationally displaced inside the first, second, third, and fourth linear through holes to be linearly moved.

At this time, the slot-type locking holes of the first, second, third, and fourth connected ports provided on the ends of the rotationally displaced operation bars cross each other with a phase difference of 90 degrees with respect to the locking pieces of the first, second, third, and fourth connecting ports entering into the inner cavity portions and are locked and connected to each other.

In addition, when the guide pin is linearly moved along the linear slit in the linear section by the external force, the operation bars of the first, second, third, and fourth connection shafts are linearly moved inside the first, second, third, and fourth linear through holes in the state where the slot-type locking holes and the locking pieces are locked and connected to each other.

Figure 14A:
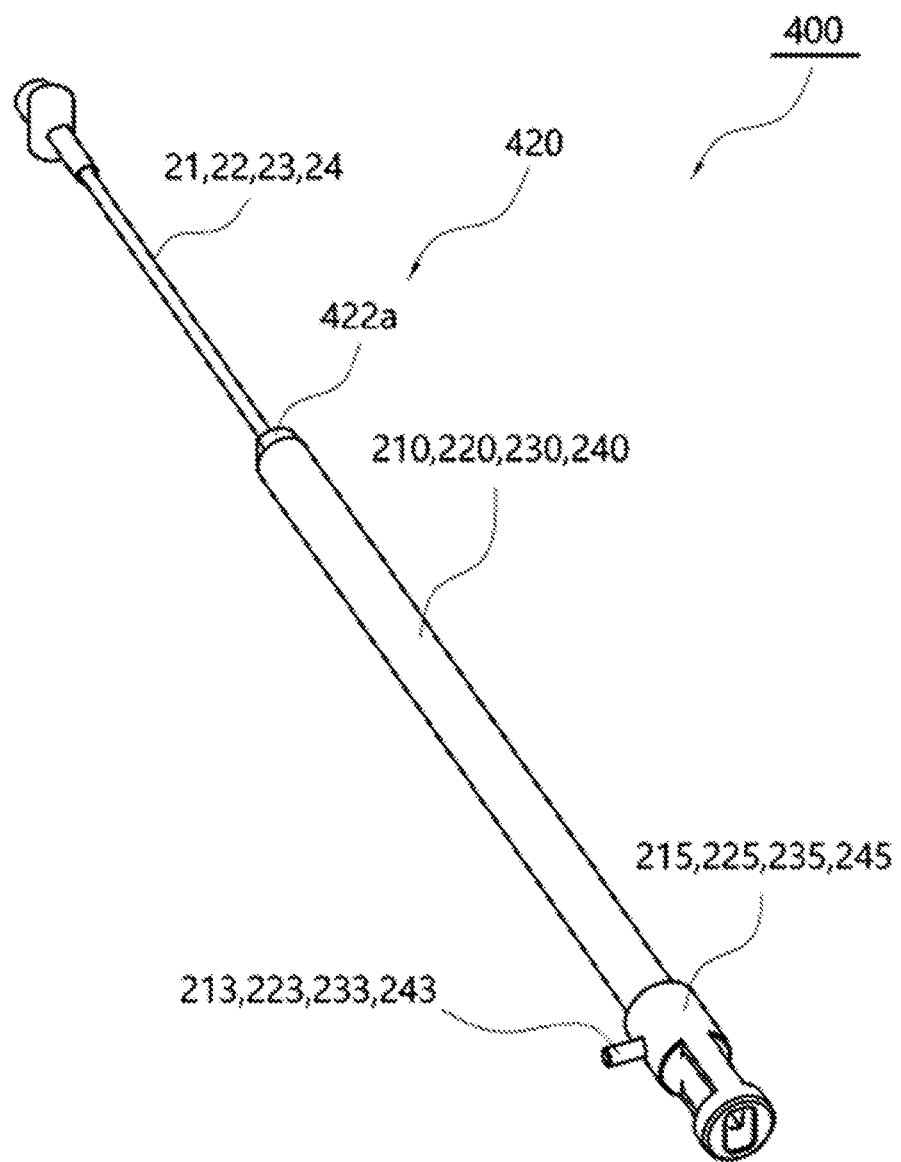
FIGS. 14A, 14B, and 14C are an assembling diagram, an exploded diagram, and a cross-sectional diagram illustrating a second buffer part provided in the detachable endoscope having the wire buffer function according to the exemplary embodiment of the present disclosure.
Figure 14B:
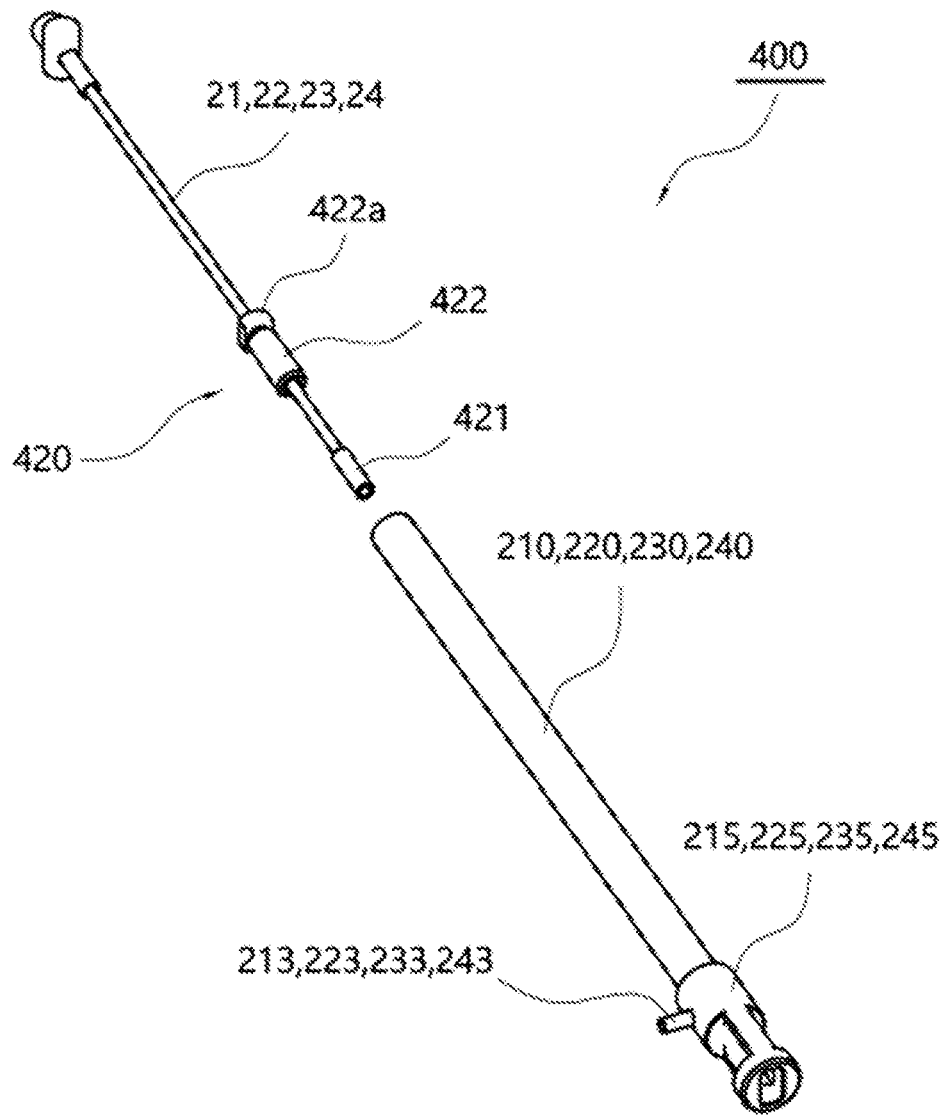
Figure 14C:
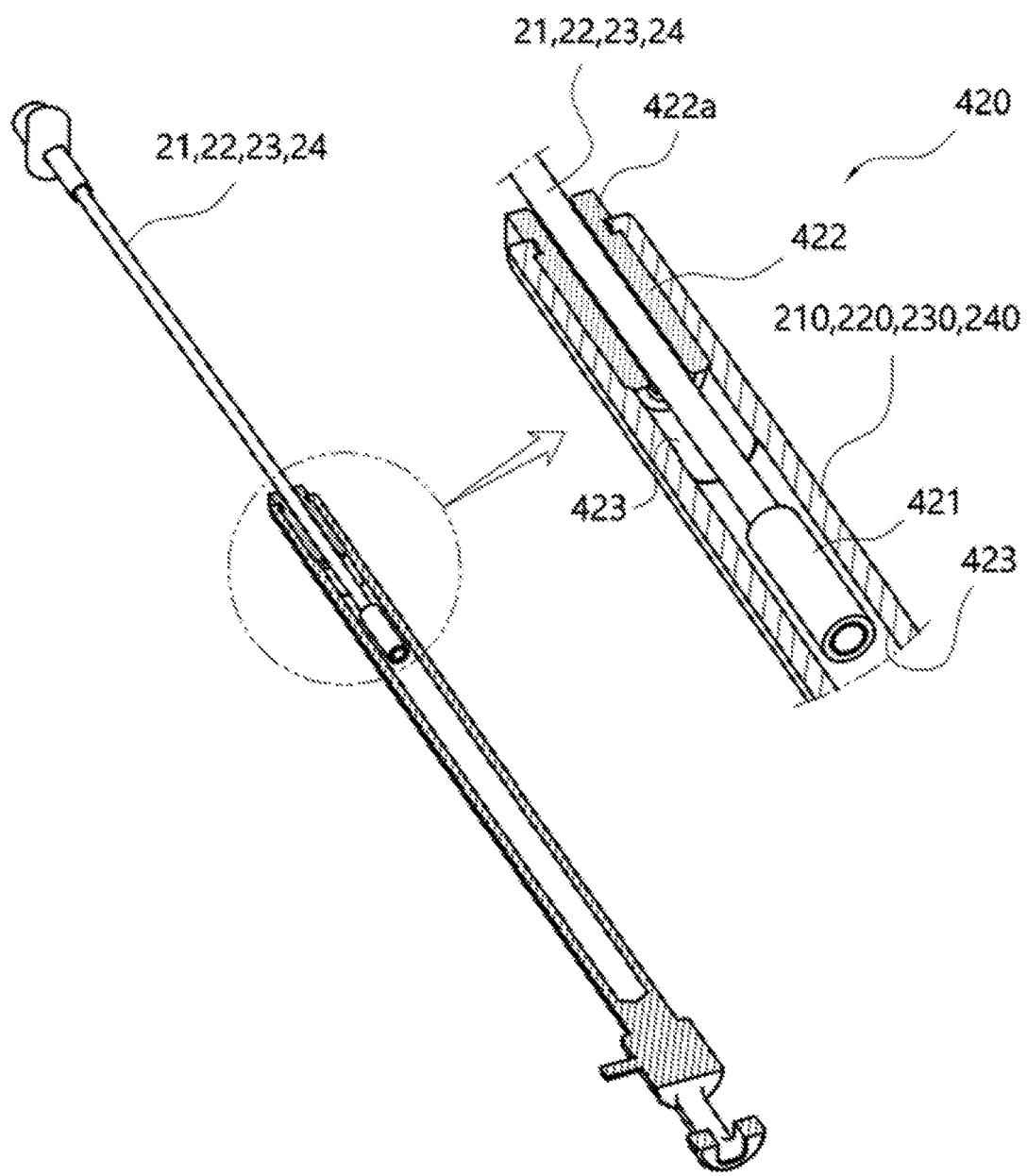

As illustrated in FIGS. 14A, 14B, and 14C, the second buffer part 420 gives a buffer function to a portion connecting the first, second, third, and fourth connection wires 21, 22, 23, 24 provided inside the operation part 20 and the first, second, third, and fourth connection shafts 210, 220, 230, 240 provided in the second detachable module 200 so that the connected port of any one of the first, second, third, and fourth connection shafts 210, 220, 230, 240 selectively pulled and moved and the connecting port of any one of the first, second, third, and fourth rack gears 110, 120, 130, 140 corresponding thereto are smoothly locked and connected to each other.

The second buffer parts 420 include second buffer bodies 421 having substantially cylindrical shapes integrally provided on the ends, which are the respective front ends of the first, second, third, and fourth connection wires 21, 22, 23, 24, and form second buffer line holes 423 having predetermined lengths formed to be opened to the outside inside the respective one ends of the first, second, third, and fourth connection shafts 210, 220, 230, 240.

Therefore, the second buffer body 421 entering into and disposed in the opened end of the second buffer line hole 423 having one end closed is moved inside the second buffer line hole in conjunction with the movements of the first, second, third, and fourth connection wires 21, 22, 23, 24.

The opened ends of the respective second buffer line holes formed to be opened to the outside on one ends of the first, second, third, and fourth connection shafts 210, 220, 230, 240 have second buffer stoppers 422, which have hollow cylindrical shapes formed to have the inner holes penetrating the body, correspondingly inserted and fixedly installed therein so that the connection wire having the second buffer body 421 freely passes in order to prevent the second buffer body from being separated to the outside.

The outer ends of the second buffer stoppers 422 are preferably provided with protrusions 422a having planar portions exposed to the ends of the first, second, third, and fourth connection shafts so as to facilitate the work of separating the second buffer stoppers assembled inside the second buffer line holes to the outside.

The inner surface of the opened end of the second buffer line hole 423 has a second inner projection 423a having an annular shape formed to protrude therefrom so as to form a circular hole through which the second buffer body 421 may pass while preventing the excessive inner entry by contacting the end of the second buffer stopper.

Therefore, the second buffer bodies provided on the respective ends of the first, second, third, and fourth connection wires penetrating the inner holes of the second buffer stoppers are reciprocatably inserted into and disposed in the second buffer line holes formed in the respective ends of the first, second, third, and fourth connection shafts, and the second buffer stoppers are screw-coupled and fixedly installed to male screw parts formed on the inner surfaces of the second buffer line holes, so that the second buffer bodies are linearly moved without locking in conjunction with the any one of the first, second, third, and fourth connection wires in the buffer sections of the second buffer line holes without being separated to the outside by the locking with the front ends of the second buffer stoppers or generate locking forces by contacting the second buffer stoppers.

According to the second buffer part 420 having the above configuration, one of the first, second, third, and fourth connection shafts upon selective rotation of the operation part may be pulled and moved toward the operation part by the interference between the second buffer body and the second buffer stopper, and the remaining connection shafts may stand by and stop inside the front end of the operation part, thereby individually and smoothly performing the selective locking-connection between any one of the first, second, third, and fourth connecting ports of the first detachable module and any one of the first, second, third, and fourth connected ports of the second detachable module.

Figure 15A:
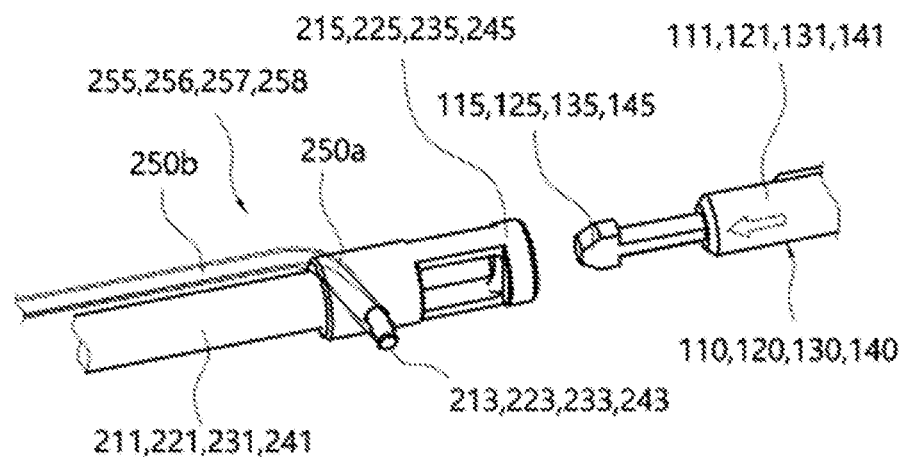
FIGS. 15A, 15B, and 15C are diagrams illustrating operation states of the second detachable module operated in conjunction with the second buffer part provided in the detachable endoscope having the wire buffer function according to the exemplary embodiment of the present disclosure.

As illustrated in FIG. 15A, the selective locking-connection between the first, second, third, and fourth connected ports of the second detachable module 200 and the first, second, third, and fourth connecting ports of the first detachable module 100 is configured so that the slot-type locking holes of the first, second, third, and fourth connected ports provided on the ends of the first, second, third, and fourth connection shafts and the locking pieces of the first, second, third, and fourth connecting ports provided on the ends of the first, second, third, and fourth rack gears face each other on a one-to-one basis.

At this time, the slot-type locking holes of the first, second, third, and fourth connected ports 215, 225, 235, 245 face the locking pieces of the first, second, third, and fourth connecting ports 115, 125, 135, 145 in the same vertical states.

Figure 16A:
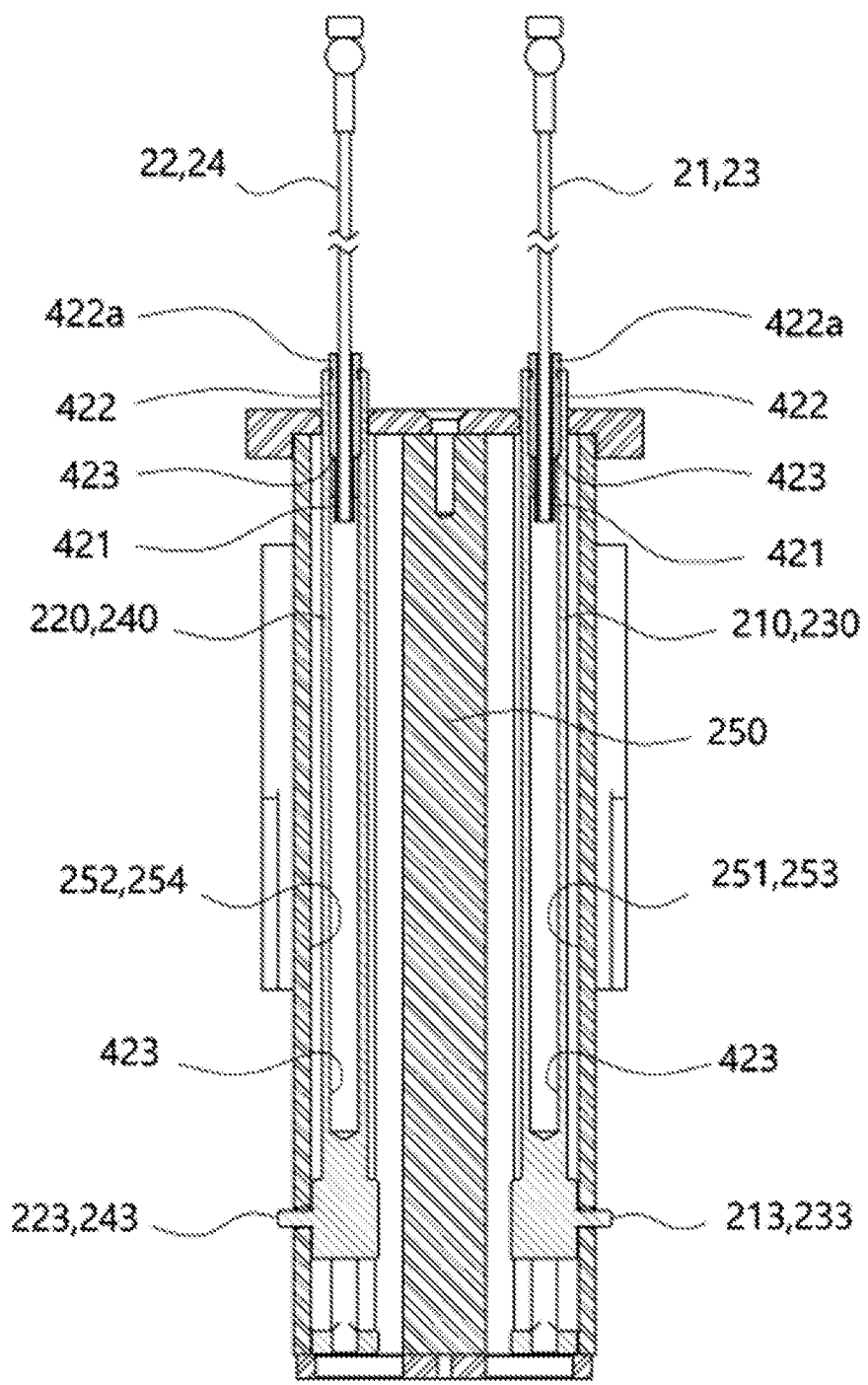
FIGS. 16A, 16B, and 16C are diagrams illustrating operation states of the second buffer part operated in conjunction with the second detachable module provided in the detachable endoscope having the wire buffer function according to the exemplary embodiment of the present disclosure.

In addition, as illustrated in FIG. 16A, the second buffer bodies 421 provided on the respective one ends of the first, second, third, and fourth connection wires stop and stand by in the second buffer line holes formed in the respective ends of the first, second, third, and fourth connection shafts so as to contact the second buffer stoppers or be disposed to be spaced apart from the second buffer stoppers.

Figure 15B:
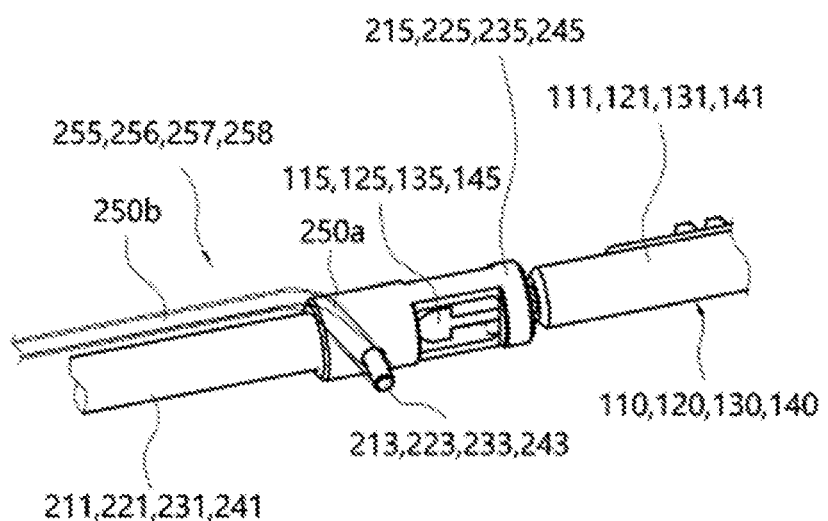

Subsequently, when the front end of the operation part having the second detachable module and the rear end of the insertion part having the first detachable module are coupled to each other, as illustrated in FIG. 15B, the locking pieces of the first, second, third, and fourth connecting ports 115, 125, 135, 145 correspondingly facing the slot-type locking holes of the first, second, third, and fourth connected ports enter into the inner cavity portions formed in the first, second, third, and fourth connected ports of the first, second, third, and fourth connection shafts without locking through the slot-type locking holes of the first, second, third, and fourth connected ports 215, 225, 235, 245 to maintain the state equally perpendicular to the vertical slot-type locking holes.

In a state where external housings are mechanically connected to the outer surfaces by the ring-type coupling body provided between the front end of the operation part and the rear end of the insertion part, the locking pieces of the first, second, third, and fourth connecting ports provided on one ends of the first, second, third, and fourth rack gears are disposed and stand by in the internal spaces of the respective inner cavity portions of the first, second, third, and fourth connected ports provided on the respective one ends of the first, second, third, and fourth connection shafts without locking.

Figure 15C:
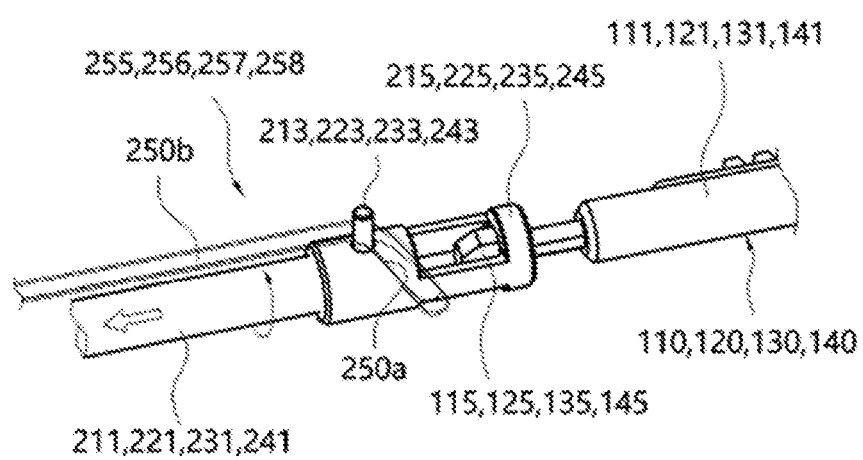

In this state, as illustrated in FIG. 15C, when any one of the upper and lower operation handles provided in the operation part is selected and rotatably operated, any one of the first, second, third, and fourth connection shafts assembled for each of the first, second, third, and fourth linear through holes formed in the main body block of the second module main body is pulled toward the operation part by the locking with the second buffer body and the second buffer stopper by the external force generated at this time and rotationally displaced while being pulled and moved in proportion with the rotational amount of the operation handle.

Figure 16B:
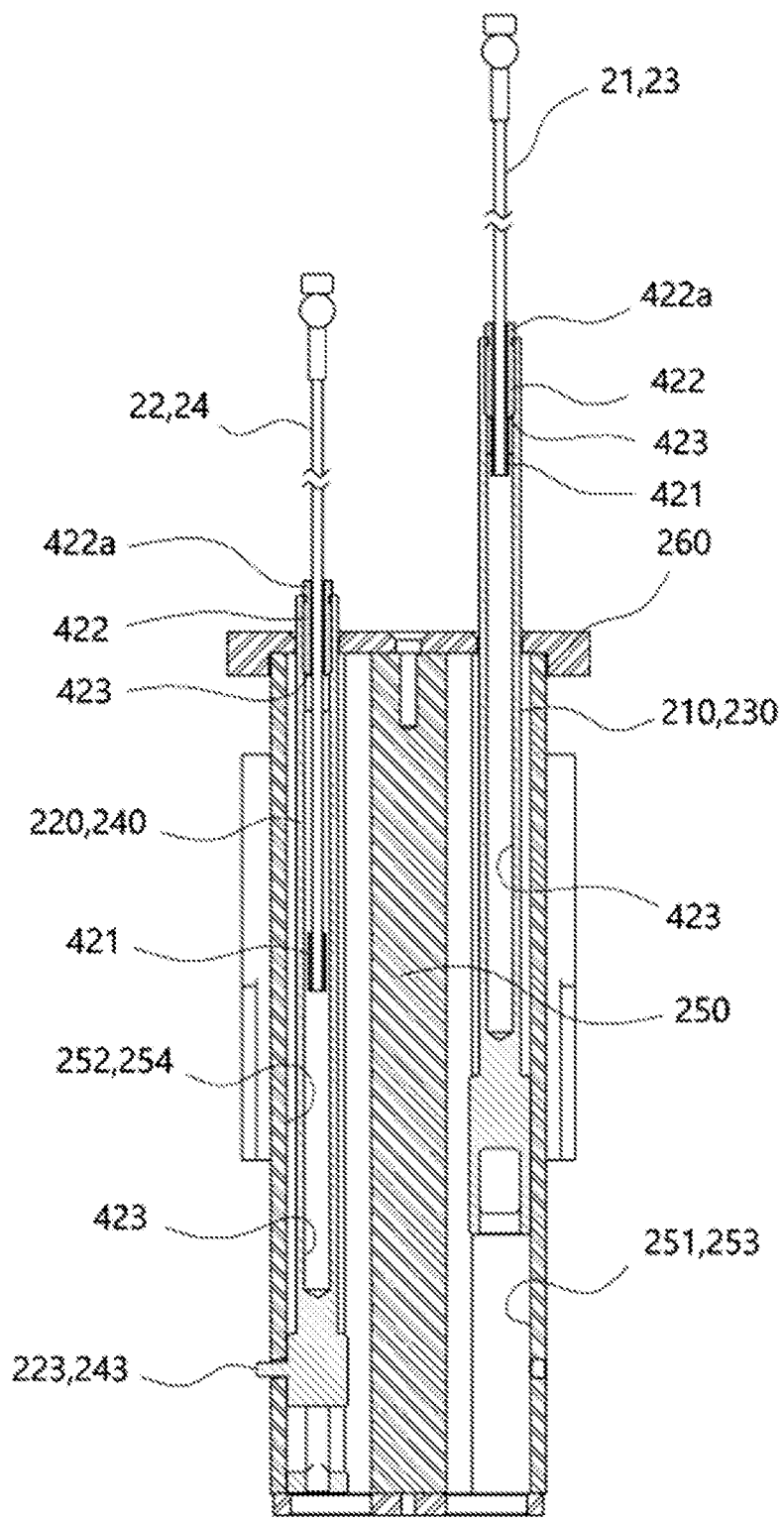
Figure 16C:
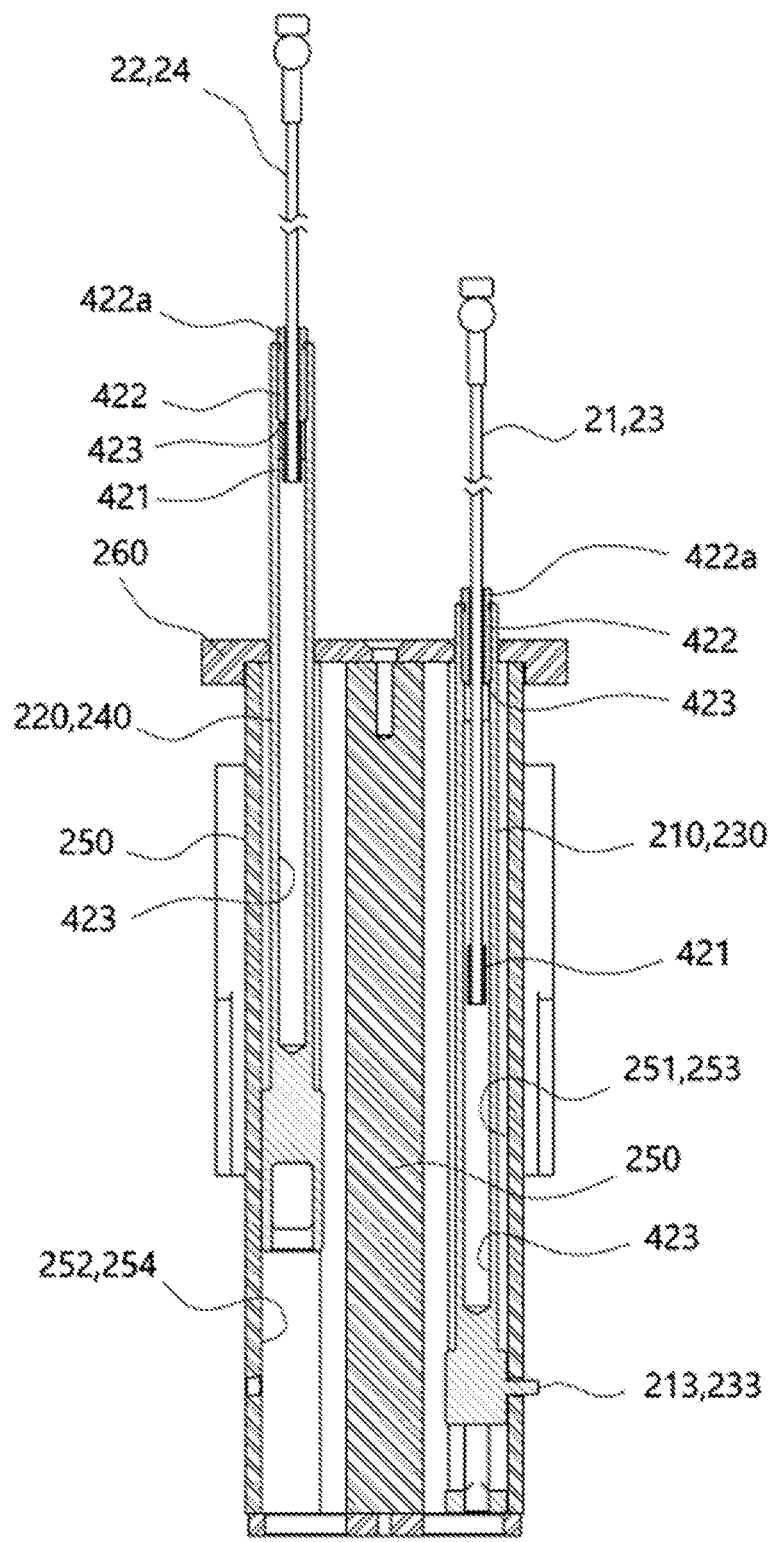

That is, as illustrated in FIGS. 16B and 16C, when any one of the first, second, third, and fourth connection wires is pulled toward the operation part by the selective rotation of the operation part, the second buffer body provided on the end of the connection wire pulled and moved toward the operation part performs the pulling movement of the corresponding connection shaft while contacting the second buffer stopper provided in the second buffer line hole.

At the same time, as illustrated in FIGS. 16B and 16C, since the second buffer body provided on the end of the connection wire pushed and moved toward the insertion part in conjunction with the connection wire pulled and moved toward the operation part by the selective rotation of the operation part is moved toward the insertion part without locking in the buffer section formed inside the second buffer line hole, the connection shaft corresponding to the connection wire pushed and moved toward the operation part maintains the initial standby state as it is.

Here, as illustrated in FIG. 15A, the connection shaft corresponding to the connection wire in which the selective rotation operation of the operation handle is not performed, and the connection shaft corresponding to the connection wire pushed and moved toward the insertion part upon selective rotational operation of the operation handle stand by in the linear through hole of the second detachable module, so that the locking piece of the connecting port is disposed in the inner cavity portion of each of the connected ports, thereby maintaining the locking standby state for locking-connection.

The locking standby state is the same state as the locking-release state where the locking piece of the connecting port and the slot-type locking hole of the connected port are not locked.

That is, when any one of the first, second, third, and fourth connection shafts is pulled toward the operation part by the external force caused by the selective rotational operation of the user and the second buffer body is in contact with the second buffer stopper, the guide pin provided on one end of the connection shaft is pulled and moved along the curve-type slit of the composite guide slits of the second module main body and the operation bar of the corresponding connection shaft is rotationally displaced by about 90 degrees unidirectionally inside the corresponding linear through hole, so that the slot-type locking holes of the first, second, third, and fourth connected ports provided on the ends of the rotationally displaced operation bars cross the locking pieces of the corresponding connecting ports which enter into and stand by in the inner cavity portions with a phase difference of about 90 degrees and the slot-type locking holes and the locking pieces are converted into the locking-connection state without requiring locking-connection means such as a button member provided separately.

Consecutively, when the selective rotational operation of the user is continuously performed, the guide pin may be moved along the linear-type slit of the composite guide slits of the second module main body to linearly move the operation bar of the corresponding connection shaft, thereby operating the front end of the insertion part to be bent in any one of the vertical direction and the horizontal direction according to the aspect of being selectively rotationally operated.

Meanwhile, in the process of being pulled to one side by the external force by the selective rotational operation of the operation part, the elastic body provided on the corresponding connection shaft pulled and moved is compressed and deformed to generate the elastic restoring force.

Therefore, when the external force caused by the selective rotational operation of the operation part is released and thus any one of the first, second, third, and fourth connection shafts pulled and moved by the elastic restoring forces of the elastic bodies is pushed toward the insertion part, the guide pin provided on one end of the connection shaft is pushed and moved reversely along the curved slit and the operation bar of the corresponding connection shaft returns by rotating about 90 degrees reversely inside the corresponding linear through hole, so that the slot-type locking holes of the first, second, third, and fourth connected ports provided on the ends of the rotationally returning operation bars return to the same vertical states as the locking pieces of the corresponding connecting ports which stand by in the vertical states inside the inner cavity portions, and converted into the locking-release state corresponding to the locking-connection standby state without requiring the locking release means, such as a button member separately provided, by the returning operation.

In this state, it is possible to completely separate the insertion part and the operation part by the simple separation release of the ring-type coupling body for coupling the rear end of the insertion part and the front end of the operation part.

The aforementioned present disclosure is not limited by the aforementioned exemplary embodiments and the accompanying drawings, and it will be apparent to those skilled in the art to which the present disclosure pertains that various substitutions, modifications, and changes are possible without departing from the technical spirit of the present disclosure.

The invention claimed is:

1. A detachable endoscope comprising:
   an operation part for operating a front end of an insertion part having an illuminating photographing part to be bent; and
   a detachable unit for detachably coupling the insertion part and the operation part,
   wherein the detachable unit comprises:
   a first detachable module connected to operation wires that are connected to the front end of the insertion part; and
   a second detachable module connected to connection wires of a direction conversion part for converting a rotational motion into a linear motion in the operation part,
   wherein the first detachable module comprises:
   a first module main body having linear guide holes formed in a longitudinal direction thereof, and having a central placement hole formed in a thickness direction thereof;
   a plurality of rack gears disposed in the linear guide holes, each rack gear being connected to the respective operation wire via a first buffer part;
   a first pinion gear engaged between first and second rack gears of the plurality of rack gears;
   a second pinion gear engaged between the third and fourth rack gears of the plurality of rack gears; and
   a gear shaft disposed in the central placement hole, the first and second pinion gears being assembled with the gear shaft,
   wherein the first buffer part comprises:
   a first buffer body connected to the respective operation wire;
   a first buffer line hole formed in the respective rack gear so as for the first buffer body to be inserted and disposed therein; and
   a first buffer stopper having an inner hole so as for the respective operation wire to be movably disposed therein and assembled to the first buffer line hole so as to prevent the first buffer body from being separated to an outside of the buffer line hole,
   wherein the first buffer stopper has a fixing part having an assembling hole such that a fastening member fastened to a fastening hole formed in an end of the respective rack gear is disposed in the assembling hole.

2. The detachable endoscope of claim 1, wherein the first buffer stopper has a hollow cylindrical body having a slit cutout in a longitudinal direction.

3. The detachable endoscope of claim 1, wherein an inner surface of an inlet end of the first buffer line hole is in contact with an end of the first buffer stopper, and has a first inner projection having an annular shape forming a circular hole through which the first buffer body passes.

4. The detachable endoscope of claim 1, wherein each of the plurality of rack gears comprises:
a linear bar having a predetermined length and slidably assembled in the respective guide hole; and
linear gear teeth formed to protrude from the linear bar so as to be gear-engaged with circular gear teeth formed on an outer circumferential surface of the respective pinion gear.

5. The detachable endoscope of claim 4, wherein the linear bar comprises a movable body guided and moved along a linear-type guide slit formed to be cutout on a side surface of the first module main body.

6. The detachable endoscope of claim 1, wherein the gear shaft has first and second ring-type grooves recessed on outer circumferential surfaces thereof corresponding to the first and second pinion gears, and the first and second ring-type grooves have first and second elastic rings elastically contacting inner circumferential surfaces and outer circumferential surfaces of the first and second pinion gears.

7. The detachable endoscope of claim 1, wherein the first detachable module comprises a wire support part for supporting linear motions of the operation wires, and
wherein the wire support part comprises:
support bodies having support holes, into which the operation wires are correspondingly inserted;
a support block for fixedly installing the support bodies thereon; and
a connection bracket for assembling the support block on one end of the first module main body.

8. A detachable endoscope comprising:
an operation part for operating a front end of an insertion part having an illuminating photographing part to be bent; and
a detachable unit for detachably coupling the insertion part and the operation part,
wherein the detachable unit comprises:
a first detachable module connected to operation wires that are connected to the front end of the insertion part; and
a second detachable module connected to connection wires of a direction conversion part for converting a rotational motion into a linear motion in the operation part,
wherein the second detachable module comprises:
a second module main body having linear through holes formed in a longitudinal direction thereof and disposed inside a front end of the operation part;
connection shafts movably disposed in the linear through holes, each connection shaft being coupled to the respective connection wire via a second buffer part; and
connected ports disposed on ends of the connection shafts and configured to be selectively locked and connected to connecting ports of the first detachable module,
wherein the second buffer part comprises:
a second buffer body connected to the respective connection wire;
a second buffer line hole formed in the respective connection shaft so as for the second buffer body to be inserted and disposed therein; and
a second buffer stopper assembled to the second buffer line hole so as to prevent the second buffer body from being separated to an outside of the buffer line hole, and
wherein upon selective rotation of the operation part one of the connection shafts is pulled and moved toward the operation part by an interference between the second buffer body and the second buffer stopper, and the remaining connection shafts stand by and stop inside the front end of the operation part, thereby selectively locking and connecting any one of the connecting ports of the first detachable module to any one of the connected ports of the second detachable module.

9. The detachable endoscope of claim 8, wherein an inner surface of an inlet end of the second buffer line hole is in contact with an end of the second buffer stopper, and has a second inner projection having an annular shape forming a circular hole through which the second buffer body passes.

10. The detachable endoscope of claim 8, wherein each of the connection shafts comprises:
an operation bar configured to be inserted into and movably disposed in the respective linear through hole, and having at least one elastic body;
guide pin provided on one end of the operation bar so as to rotationally displace the operation bar while being curvedly guided and moved along a composite guide slit formed to be cutout on the second module main body; and
a connected port provided on one end of the operation bar so as to be selectively locked and connected to the respective connecting port.

11. The detachable endoscope having the wire buffer function of claim 10,
wherein the second module main body comprises:
a main body block having the linear through holes formed therein, and having the composite guide slits formed to be cutout on an outer surface thereof;
a first cover plate having a plurality of first entry and exit holes, through which the connection shafts enter and exit and provided on one end of the main body block; and
a second cover plate having a plurality of second entry and exit holes corresponding to the linear through holes and provided on another end of the main body block.

12. The detachable endoscope having the wire buffer function of claim 11,
wherein the elastic body has one end contacting the first cover plate, and has another end contacting a large diameter portion of the operation bar in which the guide pin is provided.

13. The detachable endoscope of claim 11,
wherein the composite guide slit comprises:
a curved section composed of a curved slit curvedly extending from both side surfaces of the main body block to upper and lower surfaces thereof; and
a linear section composed of a linear slit linearly extending from the upper and lower surfaces of the main body block.

14. The detachable endoscope of claim 8,
wherein the connected ports comprise slot-type locking holes exposing inner cavity portions toward the connecting ports, and the connecting ports comprise locking pieces having front ends spread to both sides thereof.

\* \* \* \* \*